US012758544B2

(12) United States Patent
Wagner-Hattler

(10) Patent No.: US 12,758,544 B2
(45) Date of Patent: Oct. 13, 2026

(54) PHARMACEUTICAL FORMULATION

(71) Applicant: Hoffmann-La Roche Inc., Little Falls, NJ (US)

(72) Inventor: Leonie Flurina Claude Wagner-Hattler, Allschwil (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 1151 days.

(21) Appl. No.: 17/580,875

(22) Filed: Jan. 21, 2022

(65) Prior Publication Data

US 2022/0218699 A1 Jul. 14, 2022

Related U.S. Application Data

(63) Continuation of application No. PCT/EP2020/071332, filed on Jul. 29, 2020.

(30) Foreign Application Priority Data

Jul. 31, 2019 (EP) .................................... 19189386

(51) Int. Cl.

| | |
|---|---|
| ***A61K 31/496*** | (2006.01) |
| ***A61K 9/20*** | (2006.01) |
| ***A61K 9/28*** | (2006.01) |
| ***A61K 47/02*** | (2006.01) |
| ***A61K 47/10*** | (2017.01) |
| ***A61K 47/14*** | (2017.01) |
| ***A61K 47/38*** | (2006.01) |

(52) U.S. Cl.

CPC .......... *A61K 31/496* (2013.01); *A61K 9/2086* (2013.01); *A61K 9/2095* (2013.01); *A61K 9/2893* (2013.01); *A61K 47/02* (2013.01); *A61K 47/10* (2013.01); *A61K 47/14* (2013.01); *A61K 47/38* (2013.01)

(58) Field of Classification Search

CPC .. A61K 31/496; A61K 9/2086; A61K 9/2095; A61K 9/2893; A61K 47/02; A61K 47/10; A61K 47/14; A61K 47/38; A61K 9/1611; A61K 9/2018; A61K 9/2009; A61K 9/1617; A61K 9/1623; A61K 9/1652; A61K 9/2054; A61K 9/2866; A61K 9/2072; A61P 35/00

USPC ........................................................ 514/252

See application file for complete search history.

(56) References Cited

U.S. PATENT DOCUMENTS

| | | | | |
|---|---|---|---|---|
| 8,299,057 B2 | | 10/2012 | Lombardi Borgia et al. | |
| 8,673,893 B2 | | 3/2014 | Lombardi Borgia et al. | |
| 9,029,356 B2 | | 5/2015 | Lombardi Borgia et al. | |
| 9,085,558 B2 | | 7/2015 | Lombardi Borgia et al. | |
| 9,085,565 B2 | | 7/2015 | Barbugian et al. | |
| 9,382,235 B2 | | 7/2016 | Barbugian et al. | |
| 10,398,693 B2 | | 9/2019 | Codallos, Jr. et al. | |
| 10,738,037 B2 | | 8/2020 | Candiani et al. | |
| 11,007,191 B2 | | 5/2021 | Orr et al. | |
| 11,253,515 B2 | | 2/2022 | Codallos, Jr. et al. | |
| 11,337,977 B2 | * | 5/2022 | Reents | A61K 9/2059 |
| 2015/0051222 A1 | | 2/2015 | Barbugian et al. | |
| 2016/0279125 A1 | | 9/2016 | Barbugian et al. | |
| 2018/0055845 A1 | * | 3/2018 | Reents | A61K 9/2018 |
| 2019/0022089 A1 | | 1/2019 | Codallos, Jr. et al. | |

FOREIGN PATENT DOCUMENTS

| | | | | |
|---|---|---|---|---|
| WO | 2005/037287 A8 | | 6/2005 | |
| WO | 2007/008752 A2 | | 1/2007 | |
| WO | 2009/013126 A1 | | 1/2009 | |
| WO | 2013/174876 A1 | | 11/2013 | |
| WO | 2017/172602 A1 | | 10/2017 | |
| WO | 2017/202674 A1 | | 11/2017 | |
| WO | 2018/029226 A1 | | 2/2018 | |
| WO | 2019/018570 A1 | | 1/2019 | |
| WO | 2019/077506 A1 | | 4/2019 | |
| WO | 2019/110723 A1 | | 6/2019 | |
| WO | WO-2020101597 A2 | * | 5/2020 | A61K 9/48 |

OTHER PUBLICATIONS

Rozlytrek (entrectinib) capsules label 2019 retrieved from https://www.accessdata.fda.gov/drugsatfda_docs/label/2019/212725s000lbl.pdf. (Year: 2019).*

Rozlytrek® (entrectinib) oral pellets label 2023 , retrieved from https://www.accessdata.fda.gov/drugsatfda_docs/label/2023/218550Orig1s000lbl.pdf (Year: 2023).*

Handbook of Pharmaceutical Excipients "Sodium Stearyl Fumarate" (In Japanese with English version attached):762-765 (Feb. 28, 2007).

International Preliminary Report on Patentability—PCT/EP2020/071332 issued Feb. 1, 2022; pp. 1-8.

International Search Report—PCT/EP2020/071332 (w/Written Opinion),:1-13 (Oct. 29, 2020).

* cited by examiner

*Primary Examiner* — Jared Barsky

*Assistant Examiner* — Liyuan Mou

(74) *Attorney, Agent, or Firm* — Zong-Qiang Bill Tan

(57) ABSTRACT

Disclosed herein are pharmaceutical compositions and dosage forms including N-[5-(3,5-difluorobenzyl)-1H-indazol-3-yl]-4-(4-methyl-piperazin-1-yl)-2-(tetrahydro-2H-pyran-4-ylamino) benzamide that are useful in the treatment of subjects having cancer. The present disclosure also provides methods for preparing these pharmaceutical compositions and dosage forms, and methods of treating subjects having cancer utilizing the pharmaceutical compositions and dosage forms provided herein.

7 Claims, 7 Drawing Sheets

PHARMACEUTICAL FORMULATION

CROSS-REFERENCE TO RELATED APPLICATIONS

This application is a continuation of Application No. PCT/EP2020/071332, filed 29 Jul. 2020, which claims benefit of priority to EP Application No. 19189386.6 filed 31 Jul. 2019, each of which is incorporated herein by reference in its entirety.

DETAILED DESCRIPTION

The present invention relates to pharmaceutical compositions and dosage forms comprising N-[5-(3,5-difluorobenzyl)-1H-indazol-3-yl]-4-(4-methyl-piperazin-1-yl)-2-(tetrahydro-2H-pyran-4-ylamino)-benzamide, in particular wherein the pharmaceutical compositions and dosage forms are useful in the treatment of subjects having cancer. The present disclosure also provides methods for preparing these pharmaceutical compositions and dosage forms, and methods of treating subjects having cancer utilizing the pharmaceutical compositions and dosage forms provided herein. The present invention is generally directed to a patient-easier drug delivery system for targeted populations, such as pediatric and geriatric patients. Specifically, the present invention relates to a pharmaceutical composition in the form of minitablets. In particular, the present invention provides compliant dosage forms especially for patients that have difficulties to swallow, in particular in pediatric and child populations.

The compound N-[5-(3,5-difluorobenzyl)-1H-indazol-3-yl]-4-(4-methyl-piperazin-1-yl)-2-(tetrahydro-2H-pyran-4-ylamino)-benzamide and its preparation have been disclosed in U.S. Pat. No. 8,299,057, the contents of which are hereby incorporated by reference in their entirety. N-[5-(3,5-difluorobenzyl)-1H-indazol-3-yl]-4-(4-methyl-piperazin-1-yl)-2-(tetrahydro-2H-pyran-4-ylamino)-benzamide is a potent inhibitor of tyrosine kinases, NTRK1/2/3-transforming tyrosine kinase proteins (TrkA, TrkB, TrkC), proto-oncogene tyrosine-protein kinase 1 (ROS1), and anaplastic lymphoma kinase (ALK). In various in vitro studies, N-[5-(3,5-difluorobenzyl)-1H-indazol-3-yl]-4-(4-methyl-piperazin-1-yl)-2-(tetrahydro-2H-pyran-4-ylamino)-benzamide inhibited proliferation of the CRC cell line KM12, which depends upon TrkA kinase activity for proliferation and survival. It was also potent in inhibiting cell proliferation of ALK-dependent Anaplastic Large Cell Lymphoma cell lines.

WO2019018570 discloses a pharmaceutical composition comprising entrectinib in the form of a capsule.

In a single-dose food effect study in dogs of N-[5-(3,5-difluorobenzyl)-1H-indazol-3-yl]-4-(4-methyl-piperazin-1-yl)-2-(tetrahydro-2H-pyran-4-ylamino)-benzamide, in a formulation that did not comprise at least one acidulant, exposure levels of N-[5-(3,5-difluorobenzyl)-1H-indazol-3-yl]-4-(4-methyl-piperazin-1-yl)-2-(tetrahydro-2H-pyran-4-ylamino)-benzamide in the dogs were approximately 2-fold higher under fed conditions compared to those observed under fasting conditions. Such food effects can cause difficulty during human testing of drugs as the fed or fasted condition of the patient can cause exposure or bioavailability of drugs to vary widely.

In early clinical studies in humans, N-[5-(3,5-difluorobenzyl)-1H-indazol-3-yl]-4-(4-methyl-piperazin-1-yl)-2-(tetrahydro-2H-pyran-4-ylamino)-benzamide has been shown to have antitumor effects in patients having various forms of cancer having at least one molecular alteration in one or more of ALK, ROS1, TrkA, TrkB and TrkC.

The goal of any drug delivery system is to provide a therapeutic amount of drug to the proper site in the body to achieve and then maintain the desired drug concentration. The most convenient and commonly employed route of drug delivery has historically been by solid oral dosage forms, particularly tablets and capsules. However, conventional tablets and capsules are limited by their rigid dose content. Furthermore, difficulty swallowing tablets and capsules is a problem for many patients, in particular to with pediatric population, and can lead to a variety of adverse events and patient noncompliance with treatment regimens.

Lactose-free formulations are interesting to cope with potential lactose intolerances in patients.

The present invention shows surprisingly less sticking issues in the manufacturing process. Furthermore, the present invention has surprisingly improved flowability.

The flowability was surprisingly overcome by incorporation of colloidal silicon dioxide intragranularly and extragranularly in combination with mannitol extragranularly. The flowability for instance went from a FFC of the adult formulation (example 7) of 4.26 to 8.93 for the present invention.

Furthermore, according to the present invention the core tablet formulation disintegrates surprisingly fasts. The presence of Croscarmellose sodium in the intragranular as well as in the extragranular phase is responsible for this fast disintegration.

The challenges linked to the tableting process, especially the sticking issues were surprisingly overcome by the use of sodium stearyl fumarate intragranularly and magnesium stearate extragranularly as they were acting synergistically.

There exists a need in the art for improved drug delivery systems for use in patient populations having an inability to swallow tablets and capsules, e.g., pediatric and geriatric populations. Specifically, there exists a need in the art for novel entrectinib formulations. Even more specifically, there exists a need in the art for novel entrectinib multiparticulates dosage form, in particular minitablets, pellets or granules dosage forms, more particularly minitablet dosage forms, having precise pharmacologic and pharmacokinetic properties.

Standard coatings are usually being used to reduce dust, handling with care, esthetic features and distinguish between dose strength. They are not appropriate for use with entrectinib compositions as they are fast release and not masking the bitter taste of the drug. The present invention overcome these issues by having a film coating that is pH independent and release the drug at appropriate time. Therefore, for instance tap water pH variation is not affecting onset of drug release. These issues are particularly relevant for pediatric patients knowing that N-[5-(3,5-difluorobenzyl)-1H-indazol-3-yl]-4-(4-methyl-piperazin-1-yl)-2-(tetrahydro-2H-pyran-4-ylamino)-benzamide, also known as entrectinib, has bitter taste. These bitter taste are known to be problematic for patient adherence. Therefore, in an another embodiment the present invention provides a film coating for N-[5-(3,5-difluorobenzyl)-1H-indazol-3-yl]-4-(4-methyl-piperazin-1-yl)-2-(tetrahydro-2H-pyran-4-ylamino)-benzamide that is pH independent.

Figure 1:
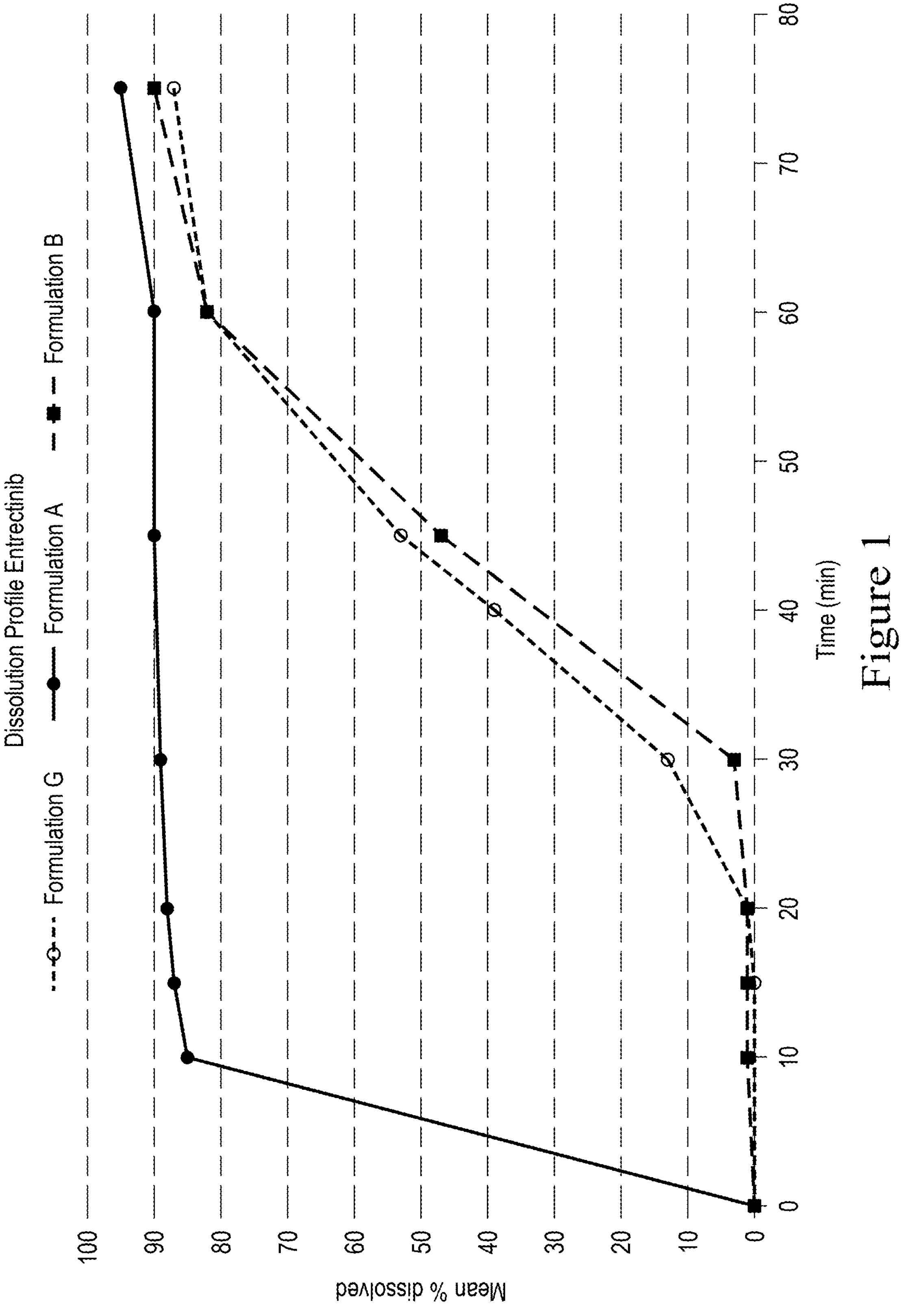
FIG. 1: Dissolution profile of entrectinib of Formulation A, Formulation B and Adult formulation (Formulation G)
Figure 2:
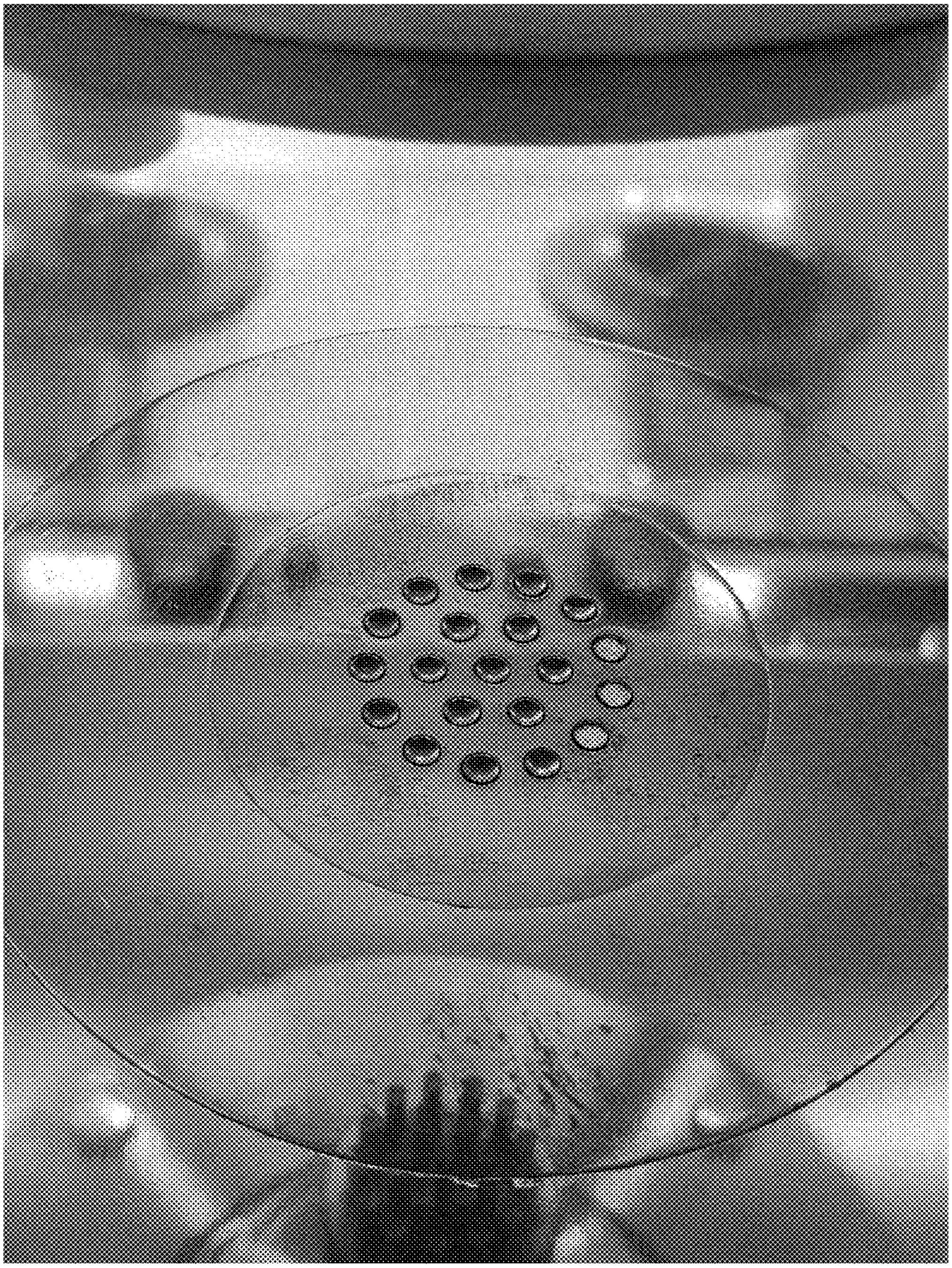
FIG. 2: Depiction of Formulation C sticking on punches.
Figure 3:
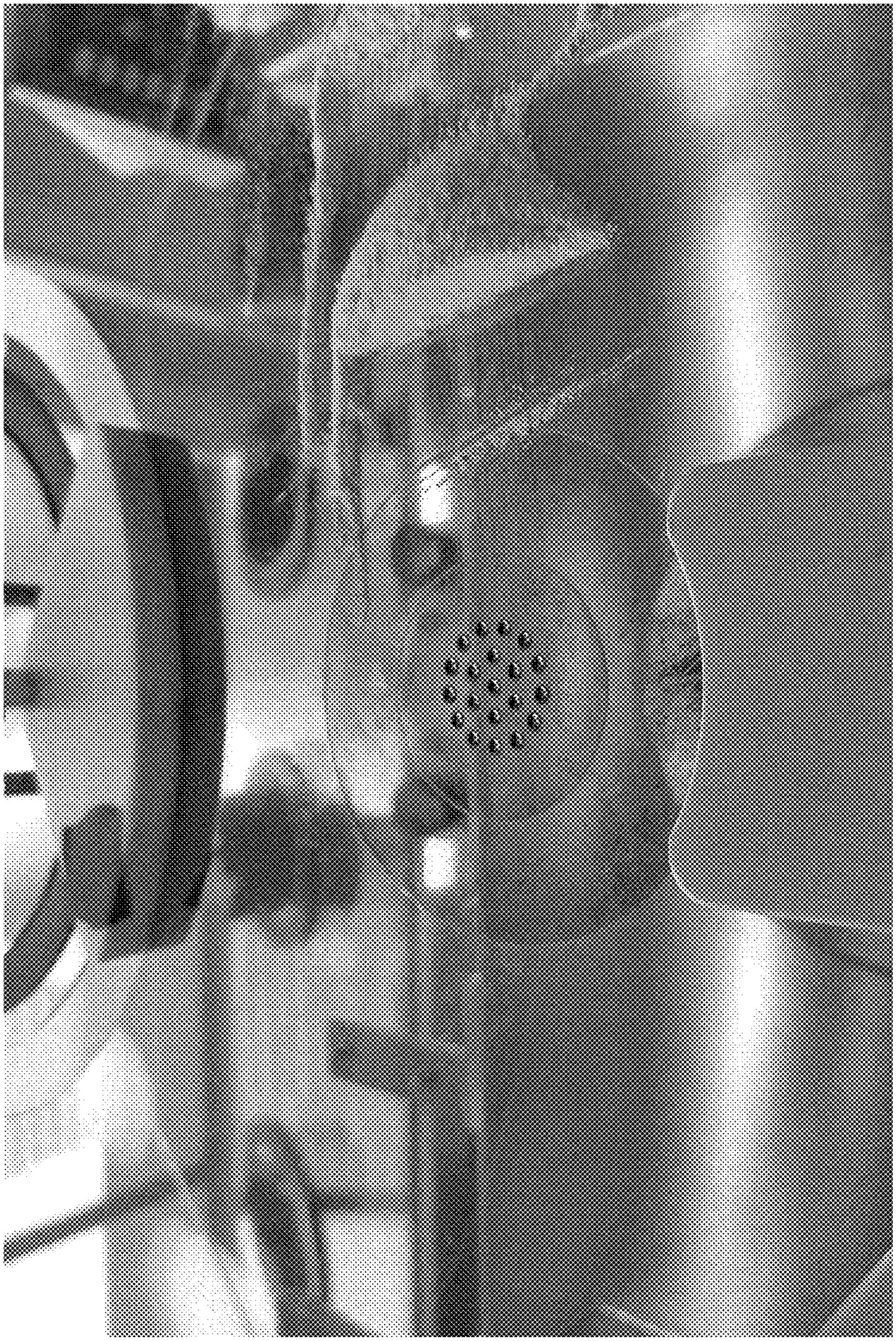
FIG. 3: Depiction of Formulation D without sticking on punches.
Figure 4:
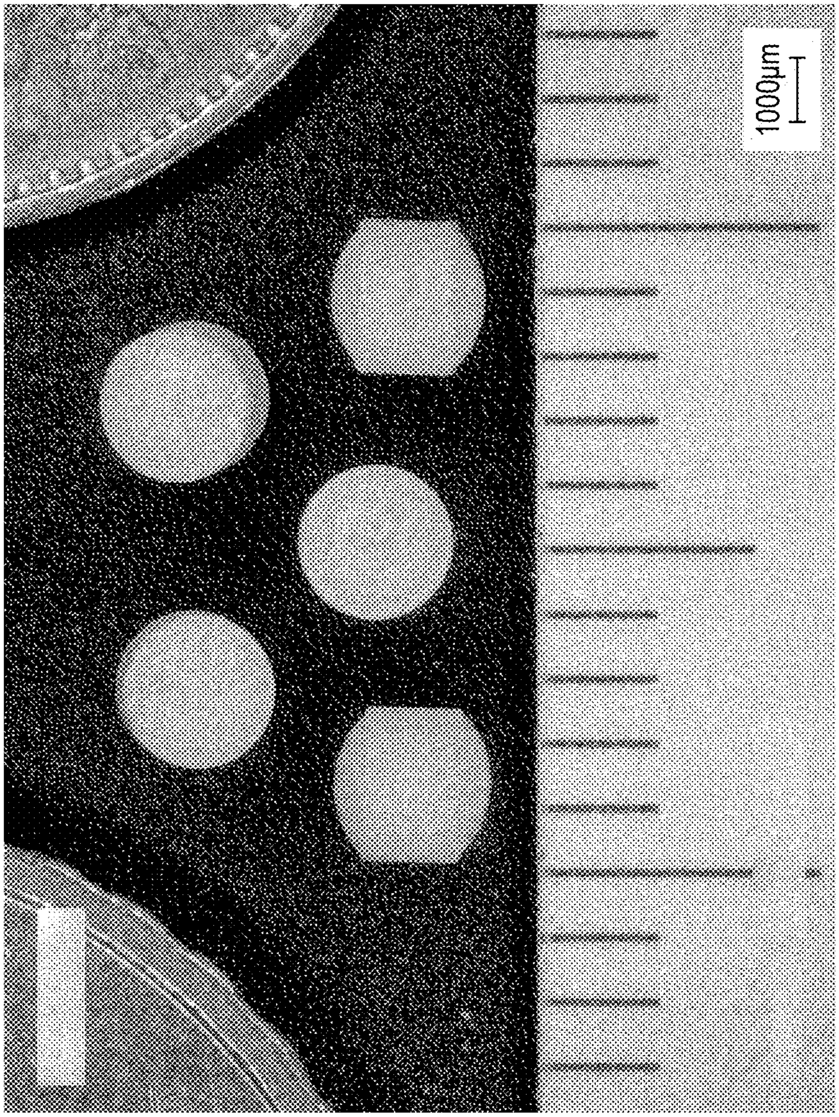
FIG. 4: Minitablets of Formulation B

The nomenclature used in the present application is based on IUPAC systematic nomenclature, unless indicated otherwise.

Various features and embodiments of the present invention are disclosed herein, however other features of the invention, modifications and equivalents will be apparent to a person skilled in the relevant art, based on the teachings provided. The invention described is not limited to the examples and embodiments provided, various alternatives equivalents will be appreciated by those skilled in the art. As used herein, the singular forms "a", "an" and "the" include the plural unless the context clearly dictates otherwise. For example, "a" individual will also include "individuals".

Unless otherwise defined, all technical and scientific terms used in the specification and claims have the same meaning as commonly understood by one of ordinary skill in the art to which this invention belongs. Although methods and materials similar or equivalent to those described herein can be used in the practice or testing of the invention, suitable methods and materials are described below.

The term "API" refers to active substance which is according to the invention entrectinib.

The term "N-[5-(3,5-difluorobenzyl)-1H-indazol-3-yl]-4-(4-methyl-piperazin-1-yl)-2-(tetrahydro-pyran-4-ylamino)-benzamide" refers a compound having Chemical Abstracts Service Registry No. 1108743-60-7 and having the chemical structure:

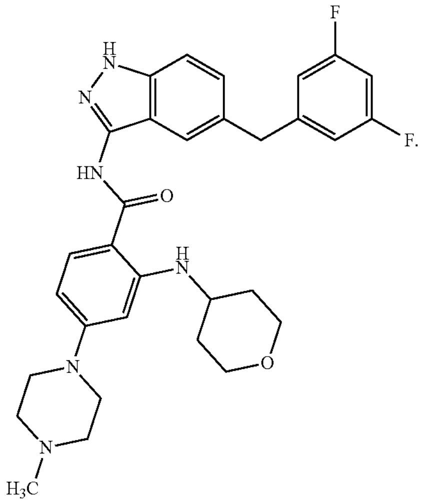 [SMILES: CN1CCN(c2ccc(C(=O)Nc3n[nH]c4ccc(Cc5cc(F)cc(F)c5)cc34)c(NC3CCOCC3)c2)CC1]

"N-[5-(3,5-difluorobenzyl)-1H-indazol-3-yl]-4-(4-methyl-piperazin-1-yl)-2-(tetrahydro-pyran-4-ylamino)-benzamide" is also known by its INN name entrectinib and can be used interchangeably. In a particular embodiment, N-[5-(3,5-difluorobenzyl)-1H-indazol-3-yl]-4-(4-methyl-piperazin-1-yl)-2-(tetrahydro-pyran-4-ylamino)-benzamide is a solid in crystalline or amorphous form, more particularly in crystalline form, even more particularly in form A or C, most particularly in form C. Form A of entrectinib has been disclosed in application W02013/174876 as "Form 2" together with a process for its preparation. Form C of entrectinib has been disclosed in application WO 2017/202674 as "Form 4" together with a process for its preparation.

Hereinafter all references to N-[5-(3,5-difluorobenzyl)-1H-indazol-3-yl]-4-(4-methyl-piperazin-1-yl)-2-(tetrahydro-pyran-4-ylamino)-benzamide herein include references to solvates, complexes, polymorphic forms, stereoisomers, and isotopically labeled versions thereof. Also included within the scope provided herein are pharmaceutical compositions comprising solvates, complexes, polymorphic forms, stereoisomers, and isotopically labeled versions of N-[5-(3,5-difluorobenzyl)-1H-indazol-3 -yl]-4-(4-methyl-piperazin-1-yl)-2-(tetrahy dro-pyran-4-ylamino)-benzamide. In particular, the present invention As used herein, the term "about" means either within plus or minus 10% of the provided value, or rounded to the nearest significant figure, in all cases inclusive of the provided value. Where ranges are provided, they are inclusive of the boundary values.

As used herein, the term "acidulant" means a chemical compound that is acidic in nature. As used herein, the term "organic acidulant" means an acidulant the chemical composition of which contains carbon. As used herein, the term "inorganic acidulant" means an acidulant the composition of which does not contain carbon.

As used herein, the terms "administration" and "administering" mean the delivery of a bioactive composition or formulation to a subject by an administration route including, but not limited to, oral, intravenous, intra-arterial, intramuscular, intraperitoneal, subcutaneous, intramuscular, topically, or combinations thereof. In some embodiments, the administration to a subject is oral.

As used herein, the term "admixture" means a mixture of one or more chemical compounds in a composition. It is understood by one having ordinary skill in the art that the pharmaceutical compositions disclosed herein comprise an admixture of N-[5-(3,5-difluorobenzyl)-1H-indazol-3-yl]-4-(4-methyl-piperazin-1-yl)-2-(tetrahydro-pyran-4-ylamino)-benzamide and the at least one acidulant.

As used herein, the term "ALK" means anaplastic lymphoma kinase receptor or CD246 (cluster of differentiation 246), which is an enzyme that in humans is encoded by the ALK gene and also has the UniProt identified ALK_HUMAN.

As used herein, the term "AUC" means the area under the curve of a plot of the concentration of a compound in the plasma of a subject versus time.

As used herein, the term "betaine hydrochloride" means a compound having Chemical Abstracts Service Registry No. 590-46-5 and the common names 1-carboxy-n,n,n-trimethylmethanaminium chloride and (carboxymethyl) trimethylammonium hydrochloride.

As used herein, the term "stickpack" refers to a small, sealed packet containing a quantity of material, which is a single-use or unit dose quantity.

As used herein, the term "biological sample," means a sample obtained from an organism that may be used in a diagnostic or monitoring assay. The sample may be of a healthy tissue, diseased tissue or tissue suspected of being diseased tissue. The sample may be a biopsy taken, for example, during a surgical procedure. The sample may be collected via means of fine needle aspiration, scraping or washing a cavity to collects cells or tissue therefrom. The sample may be of a tumor such as, for example, solid and hematopoietic tumors as well as of neighboring healthy tissue. The sample may be a smear of subject cells or a tissue section. The term encompasses blood and other liquid samples of biological origin, solid tissue samples, such as a biopsy specimen or tissue cultures or cells derived therefrom and the progeny thereof The term encompasses samples that have been manipulated in any way after their procurement, such as by treatment with reagents, solubilization, or enrichment for certain components. The term encompasses clinical samples, and also includes cells in cell culture, cell supernatants, cell lysates, cell extracts, cell homogenates, and subcellular components including synthesized proteins, serum, plasma, bodily and other biological fluids, and tissue samples. The biological sample can contain compounds that are not naturally intermixed with the cell or tissue in nature such as preservatives, anticoagulants, buffers, fixatives, nutrients, antibiotics or the like. In some embodiments, the sample is preserved as a frozen sample or as formaldehyde- or paraformaldehyde-fixed paraffin-embedded (FFPE) tissue preparation. For example, the sample can be embedded in a matrix, e.g., an FFPE block or a frozen sample.

As used herein, the term "$C_{max}$" means the peak concentration that a compound achieves in the plasma of a subject after the compound, or a pharmaceutical composition comprising the compound, has been administrated to the subject. In some embodiments, the compound, or a pharmaceutical composition comprising the compound, is administered orally to a subject to achieve a particular $C_{max}$.

The term "flowability", as used herein, is meant to mean and include the ability of a material to move smoothly from one location to another without excessive force, particularly with regard to a powder. The flowability of loose material, in particular of a powder, can be determined by its Flow Factor Coefficient (FFC). The FFC values are known to the skilled person and are also described for example in the article by Dietmar Schulze "Zur Fließfähigkeit von Schüttgüterm—Definition and Meßverfahren", published in the joumal "Chemie Ingenieur Technik" by Wiley VCH, 1995, Volume 67, Issue 1, pages 60-68, or in "Powders and Bulk Solids—Behavior, Characterization, Storage and Flow" by Dietmar Schulze, Springer-Verlag Berlin Heidelberg, 2008. The FFC values could be obtained according to http://www.uspbpep.com/usp29/v29240/usp29nf24s0_c1174.htmlit as a USP method as well as a Pheur method. For example, the FFC value can be determined by a uniaxial compression test. In the uniaxial compression test, normally a hollow cylinder, ideally with frictionless walls, is filled with the loose material, in particular with the powder, to be investigated and a stress $\sigma_1$—the consolidation stress - is applied in the vertical direction in the first step. Subsequently, the specimen is relieved of the consolidation stress $\sigma_1$, and the hollow cylinder is removed. Then, an increasing vertical compressive stress is applied onto the consolidated cylindrical loose material specimen, in particular the consolidated powder specimen, up to the stress $\sigma_c$ at which the cylindrical specimen breaks (or fails). The stress $\sigma_c$ can be called compressive strength or unconfined yield strength. The failure of the consolidated cylindrical specimen upon application of the stress $\sigma_c$ indicates incipient flow of the consolidated loose material, in particular the consolidated powder. The FFC value can then be determined as the ratio $FFC=\sigma_c/\sigma_1$.

The terms "cancer" or "tumor" may be used interchangeably, refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells can exist alone within an animal, or can be a non-tumorigenic cancer cell, such as a leukemia cell. These terms include a solid tumor, a soft tissue tumor, or a metastatic lesion. As used herein, the term "cancer" includes premalignant, as well as malignant cancers. In certain embodiments, the cancer is a solid tumor, a soft tissue tumor, or a metastatic lesion. The terms also refer to solid tumors named for the type of cells that form them, cancer of blood, bone marrow, or the lymphatic system. Examples of solid tumors include, but are not limited to, sarcomas and carcinomas. Examples of cancers of the blood include, but are not limited to, leukemias, lymphomas and myeloma. The terms include, but are not limited to, a primary cancer that originates at a specific site in the body, a metastatic cancer that has spread from the place in which it started to other parts of the body, a recurrence from the original primary cancer after remission, and a second primary cancer that is a new primary cancer in a person with a history of previous cancer of different type from latter one. As used herein "cancer" refers to any malignant and/or invasive growth or tumor caused by abnormal cell growth.

The term "multiparticulate" refers to a dosage form comprising a multiplicity of particles whose totality represents the intended therapeutically useful dose of entrectinib.

A term like "x±y %" means the range from x %–y % to x % +y %. An example is 5±1% means the range from 4% (incl.) to 6% (incl.).

A term like "x±y % by weight" in context with any disintegrant, filler, glidant, lubricant and/or entrectinib refers to "x±y % by weight" of the Tablet core total weight (this total weight is the pharmaceutical composition without the film coating weight) For example, 50 mg of entrectinib in a tablet kernel of 200 mg is 25% by weight of entrectinib of the total kernel weight.

A term like "x±y % by weight" in context with any coating agent, colourant, plasticizer and/or anti-tacking agent refers to "x±y % by weight" of the film coating's total weight. For example, 1.5 mg titanium dioxide in the tablet's coating of 6 mg is 25% by weight of the total weight of the "film coating system", "film coat" or "coating system". The term "chemotherapeutic agent", refers to a chemical substance, such as a cytotoxic or cytostatic agent, that is used to treat a condition, particularly cancer.

The term "Dry granulation" refers to a process which involves blending the ingredients followed by compaction and size reduction of the mix in order to produce a granular blend of uniform size. The dry granulation generally involves the granulation of powder mixture by compression without the use of heat and solvent. Preferably, dry granulation will be carried out at a temperature of from about ambient to about 45° C., and more preferably from about 20 ° C. to about 30° C. A particular "dry granulation" process is a "roller compaction" referring to a process of using a roller compactor to compress mixtures of materials (e.g. solids) at high pressures.

As used herein, the term "particle size distribution" or "PSD" means the relative proportions of particles of a compound having a given particle size. While the particle size of a spherical object can be unambiguously and quantitatively defined by its diameter, particles comprising an active pharmaceutical ingredient or an excipient may be non-spherical and irregular in shape. There are several methods by which those of ordinary skill in the art measure and express the size of non-spherical and irregular particles, such as measuring the size of such particles using laser diffractometry and expressing the size of such particles based on replacing a given particle with an imaginary sphere that has one of a number of properties of the particle. Such properties can be selected from, for example, but are not limited to, the diameter of an imaginary sphere having the same volume of the particle being measured (volume-based particle size), the diameter of an imaginary sphere having the same weight as the particle being measured (weight-based particle size), and the diameter of an imaginary sphere having the same surface area as the particle being measured (area-based particle size). Those having ordinary skill in the art are familiar with such methods, and the manner in which the results of such methods are expressed, and such methods can be applied to the embodiments disclosed herein without undue experimentation. The particle size distribution may be represented, for example, graphically as a plot. A common type of plot is a cumulative undersize plot which represents the fraction (e.g. by number, volume or mass) of particles that are smaller than the stated particle size. According to the present invention the PSD is being measure by Laser diffraction.

As used herein, the parameters Dv10, Dv50 and Dv90 represent the particle size at the 10%, 50%, 90% of the cumulative number or volume undersize particle size distribution. Thus, a "Dv10" for a material represents a particle size wherein 10% of the number or volume of the material consists of particles having a particle size equal to the Dv10 value or smaller. A "Dv50" for a material represents a particle size wherein 50% of the number of volume of the material consists of particles having a particle size equal to the Dv50 value or smaller. A "Dv90" for a material represents a particle size wherein 90% of the number or volume of the material consists of particles having a particle size equal to the Dv90 value or smaller.

As used herein, "ROS1" means the ROS1 receptor tyrosine-protein kinase having the UniProt designation ROS1_HUMAN.

As used herein, the term "subject" means a human

"Patient" refers to humans. The term "patient" includes adults and children, and includes men and women. More particularly according to the invention patient refers to infants, children and adolescents.

As used herein, the term "$T_{max}$" means the time when the peak concentration of a compound in the plasma of a subject is reached after administration of the compound, or a pharmaceutical composition comprising the compound, to the subject.

The term "therapeutically effective amount" refers to the amount of the compound or compounds, or pharmaceutically acceptable salts thereof, being administered to a subject which will relieve to some extent one or more of the symptoms of the disorder being treated. In reference to the treatment of a cancer, a therapeutically effective amount means that amount which has the effect of (1) reducing the size of a cancer tumor, (2) inhibiting (that is, slowing to some extent, preferably stopping) cancer tumor metastasis, (3) inhibiting to some extent (that is, slowing to some extent, preferably stopping) cancer tumor growth, and/or, (4) relieving to some extent (or, preferably, eliminating) one or more symptoms associated with the cancer.

The terms "tropomyosin receptor kinase," "Trks" and "Trk" refer the family of tropomyosin receptor kinases (Trks) that are activated by peptide hormones of the neurotrophin family and include, but are not limited to, TrkA, TrkB, and TrkC. As used herein, the term "TrkA" means wild-type tropomyosin receptor kinase A having the UniProt identifier NTRK_HUMAN. As used herein, the term "TrkB" means wild-type tropomyosin receptor kinase B having the UniProt identifier NTRK2 HUMAN. As used herein, the term "TrkC" means wild-type tropomyosin receptor kinase C having the UniProt identifier NTRK3_HUMAN. TrkA, TrkB and TrkC are also referred to by those having ordinary skill in the art as Trk1, Trk2 and Trk3, respectively. A reference to TrkA is a reference to Trk1. A reference to TrkB is a reference to Trk2. A reference to TrkC is a reference to Trk3

All embodiments of present invention can be combined.

The present invention (Embodiment 1), relates to a pharmaceutical composition comprising:

a) N-[5 -(3,5 -difluorobenzyl)-1H-indazol-3 -yl]-4-(4-methyl-piperazin-1-yl)-2-(tetrahydro-2H-pyran-4-ylamino)-benzamide, also known as entrectinib,
b) Colloidal Silicon Dioxide and
c) Mannitol.

In an another embodiment (Embodiment 2), the invention relates to the pharmaceutical composition as described according to any of embodiments recited herein comprising:

1) intragranular components comprising:
    a) N-[5-(3,5-difluorobenzyl)-1H-indazol-3-yl]-4-(4-methyl-piperazin-1-yl)-2-(tetrahydro-2H-pyran-4-ylamino)-benzamide, also known as entrectinib,
    b) Colloidal Silicon Dioxide,
2) extragranular components comprising:
    a) Colloidal Silicon Dioxide and
    b) Mannitol.

In an another embodiment (Embodiment 3), the invention relates to a pharmaceutical composition comprising:

a) N-[5-(3,5-difluorobenzyl)-1H-indazol-3-yl]-4-(4-methyl-piperazin-1-yl)-2-(tetrahydro-2H-pyran-4-ylamino)-benzamide, also known as entrectinib,
b) Magnesium stearate, and
c) Sodium stearyl fumarate.

In another embodiment (Embodiment 4), the pharmaceutical composition as described according to any of embodiment recited herein comprises:

1) intragranular components comprising:
    a) N-[5-(3,5-difluorobenzyl)-1H-indazol-3-yl]-4-(4-methyl-piperazin-1-yl)-2-(tetrahydro-2H-pyran-4-ylamino)-benzamide, also known as entrectinib,
    b) Sodium stearyl fumarate
2) extragranular components comprising:
    a) Magnesium stearate.

In another embodiment (Embodiment 5), the pharmaceutical composition as described according to any of embodiments recited herein comprises:

a) N-[5-(3,5 -difluorobenzyl)-1H-indazol-3 -yl]-4-(4-methyl-piperazin-1-yl)-2-(tetrahydro-2H-pyran-4-ylamino)-benzamide, also known as entrectinib,
b) Colloidal Silicon Dioxide,
c) Mannitol,
d) Magnesium stearate, and
e) Sodium stearyl fumarate.

In another embodiment (Embodiment 6), the pharmaceutical composition as described according to any of embodiment recited herein comprises:

1) intragranular components comprising:
    a) N-[5-(3,5-difluorobenzyl)-1H-indazol-3-yl]-4-(4-methyl-piperazin-1-yl)-2-(tetrahydro-2H-pyran-4-ylamino)-benzamide, also known as entrectinib,
    b) Colloidal Silicon Dioxide,
    c) Sodium stearyl fumarate 2) extragranular components comprising:
a) Colloidal Silicon Dioxide
b) Mannitol, and
c) Magnesium stearate.

In another embodiment (Embodiment 7), the pharmaceutical composition as described according to any of embodiment recited herein comprises:

a) N-[5-(3,5-difluorobenzyl)-1H-indazol-3-yl]-4-(4-methyl-piperazin-1-yl)-2-(tetrahydro-2H-pyran-4-ylamino)-benzamide, also known as entrectinib,
b) Magnesium stearate,
c) Sodium stearyl fumarate, and
d) Croscarmellose sodium.

In another embodiment (Embodiment 8), the pharmaceutical composition as described according to any of embodiment recited herein comprises:

1) intragranular components comprising:
a) N-[5-(3,5-difluorobenzyl)-1H-indazol-3-yl]-4-(4-methyl-piperazin-1-yl)-2-(tetrahydro-2H-pyran-4-ylamino)-benzamide, also known as entrectinib,
b) Sodium stearyl fumarate
c) Croscarmellose sodium
2) extragranular components comprising:
a) Magnesium stearate, and
b) Croscarmellose sodium.

In another embodiment (Embodiment 9), the pharmaceutical composition as described according to any of embodiment recited herein comprises:

a) N-[5-(3,5-difluorobenzyl)-1H-indazol-3-yl]-4-(4-methyl-piperazin-1-yl)-2-(tetrahydro-2H-pyran-4-ylamino)-benzamide, also known as entrectinib,
b) Colloidal Silicon Dioxide,
c) Mannitol,
d) Magnesium stearate,
e) Sodium stearyl fumarate, and
f) Croscarmellose sodium.

In another embodiment (Embodiment 10), the pharmaceutical composition as described according to any of embodiment recited herein comprises:

1) intragranular components comprising:
a) N-[5-(3,5-difluorobenzyl)-1H-indazol-3-yl]-4-(4-methyl-piperazin-1-yl)-2-(tetrahydro-2H-pyran-4-ylamino)-benzamide, also known as entrectinib,
b) Colloidal Silicon Dioxide,
c) Sodium stearyl fumarate
d) Croscarmellose sodium
2) extragranular components comprising:
c) Colloidal Silicon Dioxide
d) Mannitol,
e) Magnesium stearate, and
f) Croscarmellose sodium.

In a more specific embodiment (Embodiment 11), the present invention relates to the pharmaceutical composition as described above further comprising microcrystalline cellulose.

In a more specific embodiment (Embodiment 12), is provided the pharmaceutical composition as described according to any of the embodiments mentioned herein, comprising in addition at least one acidulant. In particular, the at least one acidulant is selected from tartaric acid, maleic acid, fumaric acid, citric acid, and betaine hydrochloride. More particularly, the at least one acidulant is tartaric acid. Even more particularly, the pharmaceutical composition as described herein in addition comprises tartaric acid. Most particularly, the pharmaceutical composition as described herein in addition comprises (D) or (L) tartaric acid or a mixture thereof, more particularly (L) Tartaric acid.

In an another embodiment (Embodiment 13), the pharmaceutical composition comprises:

a) N[5-(3,5-difluorobenzyl)-1H-indazol-3-yl]-4-(4-methyl-piperazin-1-yl)-2-(tetrahydro-2H-pyran-4-ylamino)-benzamide, also known as entrectinib,
b) Colloidal Silicon Dioxide,
c) Mannitol,
d) Magnesium stearate,
e) Sodium stearyl fumarate,
f) Croscarmellose sodium, and
g) Microcrystalline cellulose.

In an another embodiment (Embodiment 14), the present invention relates to a pharmaceutical composition comprises:

1) intragranular components comprising:
a) N-[5-(3,5-difluorobenzyl)-1H-indazol-3-yl]-4-(4-methyl-piperazin-1-yl)-2-(tetrahydro-2H-pyran-4-ylamino)-benzamide, also known as entrectinib,
b) Colloidal Silicon Dioxide,
c) Sodium stearyl fumarate,
d) Croscarmellose Sodium,
e) Microcrystalline cellulose
2) extragranular components comprising:
a) Colloidal Silicon Dioxide
b) Mannitol,
c) Magnesium stearate, and
d) Croscarmellose Sodium.

In an another embodiment (Embodiment 15), the pharmaceutical composition comprises:

a) N-[5 -(3,5 -difluorobenzyl)-1H-indazol-3 -yl]-4-(4-methyl-piperazin-1-yl)-2-(tetrahydro-2H-pyran-4-ylamino)-benzamide, also known as entrectinib,
b) Colloidal Silicon Dioxide,
c) Mannitol,
d) Magnesium stearate,
e) Sodium stearyl fumarate,
f) Croscarmellose sodium,
g) Microcrystalline cellulose, and
h) tartaric acid.

In an another embodiment (Embodiment 16), the pharmaceutical composition comprises:

1) intragranular components comprising:
a) N-[5-(3,5-difluorobenzyl)-1H-indazol-3-yl]-4-(4-methyl-piperazin-1-yl)-2-(tetrahydro-2H-pyran-4-ylamino)-benzamide, also known as entrectinib,
b) Colloidal Silicon Dioxide,
c) Sodium stearyl fumarate,
d) Croscarmellose Sodium,
e) Microcrystalline cellulose,
f) tartaric acid.
2) extragranular components comprising:
a) Colloidal Silicon Dioxide
b) Mannitol,
c) Magnesium stearate, and
d) Croscarmellose Sodium.

In an another embodiment (Embodiment 17), the invention relates to the pharmaceutical composition consisting of:

a) N-[5-(3,5-difluorobenzyl)-1H-indazol-3-yl]-4-(4-methyl-piperazin-1-yl)-2-(tetrahydro-2H-pyran-4-ylamino)-benzamide, also known as entrectinib,
b) Colloidal Silicon Dioxide,
c) Mannitol,
d) Magnesium stearate,
e) Sodium stearyl fumarate, f) Croscarmellose sodium,
g) Microcrystalline cellulose,
h) tartaric acid, and
i) a pH independent film coating, in particular as defined herein.

In an another embodiment (Embodiment 18), the invention relates to the pharmaceutical composition consisting of:

1) intragranular components consisting of:
   a) N-[5-(3,5-difluorobenzyl)-1H-indazol-3-yl]-4-(4-methyl-piperazin-1-yl)-2-(tetrahydro-2H-pyran-4-ylamino)-benzamide, also known as entrectinib,
   b) Colloidal Silicon Dioxide,
   c) Sodium stearyl fumarate,
   d) Croscarmellose Sodium,
   e) Microcrystalline cellulose,
   f) tartaric acid.
2) extragranular components consisting of:
   a) Colloidal Silicon Dioxide
   b) Mannitol,
   c) Magnesium stearate, and
   d) Croscarmellose Sodium,
3) a pH independent film coating, in particular as defined herein.

A specific embodiment (Embodiment 19) of present invention relates to the pharmaceutical composition as described herein, comprising between 5% and 45% by weight of entrectinib, particularly between 15% and 35% by weight of entrectinib, more particularly 25±5% by weight of entrectinib, most particularly 25±1% by weight of entrectinib.

A specific embodiment (Embodiment 20) of present invention relates to the pharmaceutical composition as described herein, comprising between 2% and 20% by weight of mannitol, more particularly between 5% and 15% by weight of mannitol, most particularly 10±1% by weight of mannitol.

A specific embodiment (Embodiment 21) of present invention relates to the pharmaceutical composition as described herein, comprising between 0.2% and 1.2% by weight of colloidal silicon dioxide as an intragranular component and between 0.1% and 1.0% by weight of colloidal silicon dioxide as an extragranular component, more particularly between 0.5% and 1.0% by weight of colloidal silicon dioxide as an intragranular component and between 0.2% and 0.8% by weight of colloidal silicon dioxide as an extragranular component, most particularly 0.9±0.1% by weight of colloidal silicon dioxide as an intragranular component and 0.20±0.05% by weight of colloidal silicon dioxide as an extragranular component.

A specific embodiment (Embodiment 22) of present invention relates to the pharmaceutical composition as described herein, comprising between 0.1% and 2.0% by weight of magnesium stearate, more particularly between 0.25% and 1.0% by weight of magnesium stearate, most particularly 0.45±0.05% by weight of magnesium stearate.

A specific embodiment (Embodiment 23) of present invention relates to the pharmaceutical composition as described herein, comprising between 0.5% and 5% by weight of sodium stearyl fumarate, more particularly between 1.0% and 3.0% by weight of sodium stearyl fumarate, most particularly 1.8±0.2% by weight of sodium stearyl fumarate.

A specific embodiment (Embodiment 24) of present invention relates to the pharmaceutical composition as described herein, comprising between 5% and 80% by weight of microcrystalline cellulose, particularly between 20% and 60% by weight of microcrystalline cellulose, more particularly 47.5±5% by weight of by weight of microcrystalline cellulose, most particularly 47.5±1% by weight of microcrystalline cellulose.

A specific embodiment (Embodiment 25) of present invention relates to the pharmaceutical composition as described herein, comprising between 1.0% and 8% by weight of croscarmellose sodium as an intragranular component and between 0.5% and 5% by weight of croscarmellose sodium as an extragranular component, more particularly between 2.0% and 6% by weight of croscarmellose sodium as an intragranular component and between 1.0% and 3% by weight of croscarmellose sodium as an extragranular component, most particularly 4.5±0.05% by weight of croscarmellose sodium as an intragranular component and 2.25±0.05% by weight of croscarmellose sodium as an extragranular component.

A specific embodiment (Embodiment 26) of present invention relates to the pharmaceutical composition as described herein, comprising between 0.3% and 13.3% by weight of tartaric acid, more particularly between 4.42% and 10.32% by weight of tartaric acid, most particularly 7.37 ±0.5% by weight of tartaric acid.

In yet another embodiment (Embodiment 27), the invention relates to the pharmaceutical composition as described according to any of embodiments recited herein comprising:

a) between 5% and 45% by weight of, particularly between 15% and 35% by weight of, more particularly 25±5% by weight of, most particularly 25±1% by weight of N-[5-(3,5-difluorobenzyl)-1H-indazol-3-yl]-4-(4-methyl-piperazin-1-yl)-2-(tetrahydro-2H-pyran-4-ylamino)-benzamide, also known as entrectinib,
b) between 0.3% and 2.2% by weight of, more particularly between 0.7% and 1.8% by weight of, most particularly 1.10±0.15% by weight of Colloidal Silicon Dioxide and
c) between 2% and 20% by weight of, more particularly between 5% and 15% by weight of, most particularly 10±1% by weight of mannitol.

In an another embodiment (Embodiment 28), the invention relates to the pharmaceutical composition as described according to any of embodiments recited herein comprising:

1) intragranular components comprising:
   a) between 5% and 45% by weight of, more particularly between 15% and 35% by weight of, more particularly 25±5% by weight of, most particularly 25±1% by weight of N-[5-(3,5-difluorobenzyl)-1H-indazol-3-yl]-4-(4-methyl-piperazin-1-yl)-2-(tetrahydro-2H-pyran-4-ylamino)-benzamide, also known as entrectinib,
   b) between 0.2% and 1.2% by weight of, more particularly between 0.5% and 1.0% by weight of, most particularly 0.9±0.10% by weight of Colloidal Silicon Dioxide,
2) extragranular components comprising:
   a) between 0.1% and 1.0% by weight of, more particularly between 0.2% and 0.8% by weight of, most particularly 0.20±0.05% by weight of Colloidal Silicon Dioxide and
   b) between 2% and 20% by weight of, more particularly between 5% and 15% by weight of, most particularly 10±1% by weight of Mannitol.

In an another embodiment (Embodiment 29), the invention relates to the pharmaceutical composition as described according to any of embodiments recited herein comprising:

a) between 5% and 45% by weight of, more particularly between 15% and 35% by weight of, more particularly 25 ±5% by weight of, most particularly 25 ±1% by weight of N-[5-(3,5-difluorobenzyl)-1H-indazol-3-yl]-4-(4-methyl-piperazin-1-yl)-2-(tetrahydro-2H-pyran-4-ylamino)-benzamide, also known as entrectinib, b) between 0.1% and 2.0% by weight of, more particularly between 0.25% and 1.0% by weight of, most particularly 0.45 ±0.5% by weight of Magnesium stearate, and c) between 0.5% and 5% by weight of, more particularly between 1.0% and 3.0% by weight of, most particularly 1.8±0.2% by weight of Sodium stearyl fumarate.

In an another embodiment (Embodiment 30), the pharmaceutical composition as described according to any of embodiments recited herein comprising:

1) intragranular components comprising:
   a) between 5% and 45% by weight of, more particularly between 15% and 35% by weight of, more particularly 25±5% by weight of, most particularly 25±1% by weight of N-[5-(3,5-difluorobenzyl)-1H-indazol-3-yl]-4-(4-methyl-piperazin-1-yl)-2-(tetrahydro-2H-pyran-4-ylamino)-benzamide, also known as entrectinib,
   b) between 0.5% and 5% by weight of, more particularly between 1.0% and 3.0% by weight of, most particularly 1.8±0.2% by weight of Sodium stearyl fumarate
2) extragranular components comprising:
   a) between 0.1% and 2.0% by weight of, more particularly between 0.25% and 1.0% by weight of, most particularly 0.45 ±0.05% by weight of Magnesium stearate.

In an another embodiment (Embodiment 31), the pharmaceutical composition as described according to any of embodiments recited herein comprising:

a) between 5% and 45% by weight of, more particularly between 15% and 35% by weight of, more particularly 25±5% by weight of, most particularly 25±1% by weight of N-[5 -(3,5-difluorobenzyl)-1H-indazol-3-yl]-4-(4-methyl-piperazin-1-yl)-2-(tetrahydro-2H-pyran-4-ylamino)-benzamide, also known as entrectinib, b) between 0.3% and 2.2% by weight of, more particularly between 0.7% and 1.8% by weight of, most particularly 1.10±0.15% by weight of Colloidal Silicon Dioxide, c) between 2% and 20% by weight of, more particularly between 5% and 15% by weight of, most particularly 10±1% by weight of Mannitol, d) between 0.1% and 2.0% by weight of, more particularly between 0.25% and 1.0% by weight of, most particularly 0.45±0.05% by weight of Magnesium stearate, and e) between 0.5% and 5% by weight of, more particularly between 1.0% and 3.0% by weight of, most particularly 1.8±0.2% by weight of Sodium stearyl fumarate.

In an another embodiment (Embodiment 32), the pharmaceutical composition as described according to any of embodiments recited herein comprising:

1) intragranular components comprising:
   a) between 5% and 45% by weight of, more particularly between 15% and 35% by weight of, more particularly 25±5% by weight of, most particularly 25±1% by weight of N-[5-(3,5-difluorobenzyl)-1H-indazol-3-yl]-4-(4-methyl-piperazin-1-yl)-2-(tetrahydro-2H-pyran-4-ylamino)-benzamide, also known as entrectinib,
   b) between 0.2% and 1.2% by weight of, more particularly between 0.5% and 1.0% by weight of, most particularly 0.9±0.10% by weight of Colloidal Silicon Dioxide,
   c) between 0.5% and 5% by weight of, more particularly between 1.0% and 3.0% by weight of, most particularly 1.8±0.2% by weight of Sodium stearyl fumarate
2) extragranular components comprising:
   a) between 0.1% and 1.0% by weight of, more particularly between 0.2% and 0.8% by weight of, most particularly 0.20±0.05% by weight of Colloidal Silicon Dioxide
   b) between 2% and 20% by weight of, more particularly between 5% and 15% by weight of, most particularly 10±1% by weight of Mannitol, and
   c) between 0.1% and 2.0% by weight of, more particularly between 0.25% and 1.0% by weight of, most particularly 0.45±0.05% by weight of Magnesium stearate.

In an another embodiment (Embodiment 33), the pharmaceutical composition as described according to any of embodiments recited herein comprising:

a) between 5% and 45% by weight of, more particularly between 15% and 35% by weight of, more particularly 25±5% by weight of, most particularly 25±1% by weight of N[5-(3,5-difluorobenzyl)-1H-indazol-3-yl]-4-(4-methyl-piperazin-1-yl)-2-(tetrahydro-2H-pyran-4-ylamino)-benzamide, also known as entrectinib, b) between 0.1% and 2.0% by weight of, more particularly between 0.25% and 1.0% by weight of, most particularly 0.45±0.05% by weight of Magnesium stearate, c) between 0.5% and 5% by weight of, more particularly between 1.0% and 3.0% by weight of, most particularly 1.8±0.2% by weight of Sodium stearyl fumarate, and d) between 1.5% and 13% by weight of, more particularly between 3% and 9% by weight of, most particularly 6.75±0.1% by weight of Croscarmellose sodium.

In an another embodiment (Embodiment 34), the pharmaceutical composition as described according to any of embodiments recited herein comprising:

1) intragranular components comprising:
   a) between 5% and 45% by weight of, more particularly between 15% and 35% by weight of, more particularly 25±5% by weight of, most particularly 25±1% by weight of N-[5-(3,5-difluorobenzyl)-1H-indazol-3-yl]-4-(4-methyl-piperazin-1-yl)-2-(tetrahydro-2H-pyran-4-ylamino)-benzamide, also known as entrectinib,
   b) between 0.5% and 5% by weight of, more particularly between 1.0% and 3.0% by weight of, most particularly 1.8±0.2% by weight of Sodium stearyl fumarate
   c) between 1.0 and 8.0% by weight of, more particularly between 2.0% and 6.0% by weight of, most particularly 4.5±0.05% by weight of Croscarmellose sodium
2) extragranular components comprising:
   a) between 0.1% and 2.0% by weight of, more particularly between 0.25% and 1.0% by weight of, most particularly 0.45±0.05% by weight of Magnesium stearate, and
   b) between 0.5% and 5.0% by weight of, more particularly between 1.0% and 3.0% by weight of, most particularly 2.25±0.05% by weight of Croscarmellose sodium.

In an another embodiment (Embodiment 35), the pharmaceutical composition as described according to any of embodiments recited herein comprising:

a) between 5% and 45% by weight of, more particularly between 15% and 35% by weight of, more particularly 25±5% by weight of, most particularly 25±1% by weight of N-[5-(3,5-difluorobenzyl)-1H-indazol-3-yl]-4-(4-methyl-piperazin-1-yl)-2-(tetrahydro-2H-pyran-4-ylamino)-benzamide, also known as entrectinib,
b) between 0.3% and 2.2% by weight of, more particularly between 0.7% and 1.8% by weight of, most particularly 1.10±0.15% by weight of Colloidal Silicon Dioxide,
c) between 2% and 20% by weight of, more particularly between 5% and 15% by weight of, most particularly 10±1% by weight of Mannitol,
d) between 0.1% and 2.0% by weight of, more particularly between 0.25% and 1.0% by weight of, most particularly 0.45±0.05% by weight of Magnesium stearate,
e) between 0.5% and 5% by weight of, more particularly between 1.0% and 3.0% by weight of, most particularly 1.8±0.2% by weight of Sodium stearyl fumarate, and
f) between 1.5% and 13% by weight of, more particularly between 3% and 9% by weight of, most particularly 6.75±0.1% by weight of Croscarmellose sodium.

In an another embodiment (Embodiment 36), the pharmaceutical composition as described according to any of embodiments recited herein comprising:

1) intragranular components comprising:
   a) between 5% and 45% by weight of, more particularly between 15% and 35% by weight of, more particularly 25 ±5% by weight of, most particularly 25±1% by weight of N-[5-(3,5-difluorobenzyl)-1H-indazol-3-yl]-4-(4-methyl-piperazin-1-yl)-2-(tetrahydro-2H-pyran-4-ylamino)-benzamide, also known as entrectinib,
   b) between 0.2% and 1.2% by weight of, more particularly between 0.5% and 1.0% by weight of, most particularly 0.9±0.10% by weight of Colloidal Silicon Dioxide,
   c) between 0.5% and 5% by weight of, more particularly between 1.0% and 3.0% by weight of, most particularly 1.8±0.2% by weight of Sodium stearyl fumarate
   d) between 1.0 and 8.0% by weight of, more particularly between 2.0% and 6.0% by weight of, most particularly 4.5±0.05% by weight of Croscarmellose sodium
2) extragranular components comprising:
   a) between 0.1% and 1.0% by weight of, more particularly between 0.2% and 0.8% by weight of, most particularly 0.20±0.05% by weight of Colloidal Silicon Dioxide
   b) between 2% and 20% by weight of, more particularly between 5% and 15% by weight of, most particularly 10±1% by weight of Mannitol,
   c) between 0.1% and 2.0% by weight of, more particularly between 0.25% and 1.0% by weight of, most particularly 0.45±0.05% by weight of Magnesium stearate, and
   d) between 0.5% and 5.0% by weight of, more particularly between 1.0% and 3.0% by weight of, most particularly 2.25±0.05% by weight of Croscarmellose sodium.

In an another embodiment (Embodiment 37), the pharmaceutical composition as described according to any of embodiments recited herein comprising:

a) between 5% and 45% by weight of, more particularly between 15% and 35% by weight of, more particularly 25±5% by weight of, most particularly 25±1% by weight of N-[5-(3,5-difluorobenzyl)-1H-indazol-3-yl]-4-(4-methyl-piperazin-1-yl)-2-(tetrahydro-2H-pyran-4-ylamino)-benzamide, also known as entrectinib,
b) between 0.3% and 2.2% by weight of, more particularly between 0.7% and 1.8% by weight of, most particularly 1.10±0.15% by weight of Colloidal Silicon Dioxide,
c) between 2% and 20% by weight of, more particularly between 5% and 15% by weight of, most particularly 10±1% by weight of Mannitol,
d) between 0.1% and 2.0% by weight of, more particularly between 0.25% and 1.0% by weight of, most particularly 0.45±0.05% by weight of Magnesium stearate,
e) between 0.5% and 5% by weight of, more particularly between 1.0% and 3.0% by weight of, most particularly 1.8±0.2% by weight of Sodium stearyl fumarate,
f) between 1.5% and 13% by weight of, more particularly between 3% and 9% by weight of, most particularly 6.75±0.1% by weight of Croscarmellose sodium, and
g) between 5% and 80% by weight of, particularly between 20% and 60% by weight of, more particularly 47.5±5% by weight of, most particularly 47.5±1% by weight of microcrystalline cellulose.

In an another embodiment (Embodiment 38), the present invention relates to a pharmaceutical composition as described according to any of embodiments recited herein comprising:

1) An intragranular layer comprising:
   a) between 5% and 45% by weight of, more particularly between 15% and 35% by weight of, more particularly 25±5% by weight of, most particularly 25±1% by weight of N-[5-(3,5-difluorobenzyl)-1H-indazol-3-yl]-4-(4-methyl-piperazin-1-yl)-2-(tetrahydro-2H-pyran-4-ylamino)-benzamide, also known as entrectinib,
   b) between 0.2% and 1.2% by weight of, more particularly between 0.5% and 1.0% by weight of, most particularly 0.9±0.10% by weight of Colloidal Silicon Dioxide,
   c) between 0.5% and 5% by weight of, more particularly between 1.0% and 3.0% by weight of, most particularly 1.8±0.2% by weight of Sodium stearyl fumarate,
   d) between 1.0 and 8.0% by weight of, more particularly between 2.0% and 6.0% by weight of, most particularly 4.5±0.05% by weight of Croscarmellose Sodium,
   e) between 5% and 80% by weight of, particularly between 20% and 60% by weight of, more particularly 47.5 ±5% by weight of, most particularly 47.5±1% by weight of Microcrystalline cellulose
2) An extragranular layer comprising:
   a) between 0.1% and 1.0% by weight of, more particularly between 0.2% and 0.8% by weight of, most particularly 0.20±0.05% by weight of Colloidal Silicon Dioxide
   b) between 2% and 20% by weight of, more particularly between 5% and 15% by weight of, most particularly 10±1% by weight of Mannitol, c) between 0.1% and 2.0% by weight of, more particularly between 0.25% and 1.0% by weight of, most particularly 0.45±0.05% by weight of Magnesium stearate, and d) between 0.5% and 5.0% by weight of, more particularly between 1.0% and 3.0% by weight of, most particularly 2.25±0.05% by weight of Croscarmellose Sodium.

In a more particular embodiment (Embodiment 39) of the pharmaceutical composition according to any of the embodiments mentioned herein, wherein Colloidal Silicon Dioxide is hydrophilic fumed silica with surface area of 200 $m^2/g$ (i.e. CAS 7631-86-9), most particular the colloidal silicon dioxide is Aerosil® 200 sold by Evonic.

In a more particular embodiment (Embodiment 40) of the pharmaceutical composition according to any of the embodiments mentioned herein, wherein mannitol is a compressible D-mannitol (i.e. CAS 69-65-8), more particularly the mannitol contains less than 0.05% of reducing sugars as impurities due to the manufacturing process, most particularly the mannitol is Parteck® M200. The mannitol according to any of the embodiment of the invention has a D50 of 142-231 μm.

In a more particular embodiment (Embodiment 41) of the pharmaceutical composition according to any of the embodiments mentioned herein, wherein Croscarmellose Sodium has a loss on drying of ≤10%.

In a more particular embodiment (Embodiment 42) of the pharmaceutical composition according to any of the embodiments mentioned herein, wherein Sodium stearyl fumarate has a saponification value of 142.2 to 146.0, particularly has a Dv50 of 13.6 μm, more particularly sodium stearyl fumarate is Pruv®.

In a more particular embodiment (Embodiment 43) of the pharmaceutical composition according to any of the embodiments mentioned herein, wherein Microcrystalline cellulose is CAS 9004-34-6, particularly has a Dv50 between 40 and 75 μm, more particularly is Avicel® PH101.

In another embodiment (Embodiment 44), the present invention relates to a pharmaceutical composition comprising N-[5-(3,5-difluorobenzyl)-1H-indazol-3-yl]-4-(4-methyl-piperazin-1-yl)-2-(tetrahydro-2H-pyran-4-ylamino)-benzamide, also known as entrectinib, in particular wherein the composition comprising N-[5-(3,5-difluorobenzyl)-1H-indazol-3-yl]-4-(4-methyl-piperazin-1-yl)-2-(tetrahydro-2H-pyran-4-ylamino)-benzamide is as described in the present application, and a pH independent film coating In a particular embodiment (Embodiment 45) the present invention provides a pharmaceutical composition comprising N-[5-(3,5-difluorobenzyl)-1H-indazol-3-yl]-4-(4-methyl-piperazin-1-yl)-2-(tetrahydro-2H-pyran-4-ylamino)-benzamide, in particular wherein the composition comprising N-[5-(3,5-difluorobenzyl)-1H-indazol-3-yl]-4-(4-methyl-piperazin-1-yl)-2-(tetrahydro-2H-pyran-4-ylamino)-benzamide is as described in the present application, and a film coating, in particular a pH independent film coating , comprising hydroxypropyl cellulose and ethylcellulose.

In a further particular embodiment (Embodiment 46) the present invention provides a pharmaceutical composition comprising N-[5-(3,5-difluorobenzyl)-1H-indazol-3-yl]-4-(4-methyl-piperazin-1-yl)-2-(tetrahydro-2H-pyran-4-ylamino)-benzamide, in particular wherein the composition comprising N-[5-(3,5-difluorobenzyl)-1H-indazol-3-yl]-4-(4-methyl-piperazin-1-yl)-2-(tetrahydro-2H-pyran-4-ylamino)-benzamide is as described in the present application, and a pH independent film coating comprising hydroxypropyl cellulose and ethylcellulose.

In a further particular embodiment (Embodiment 47) the present invention provides a pharmaceutical composition comprising N-[5-(3,5-difluorobenzyl)-1H-indazol-3-yl]-4-(4-methyl-piperazin-1-yl)-2-(tetrahydro-2H-pyran-4-ylamino)-benzamide, in particular wherein the composition comprising N-[5-(3,5-difluorobenzyl)-1H-indazol-3-yl]-4-(4-methyl-piperazin-1-yl)-2-(tetrahydro-2H-pyran-4-ylamino)-benzamide is as described in the present application, and a pH independent film coating as defined herein wherein hydroxypropyl cellulose is incorporated into ethylcellulose.

In a further particular embodiment (Embodiment 48) the present invention provides a pharmaceutical composition comprising N-[5-(3,5-difluorobenzyl)-1H-indazol-3-yl]-4-(4-methyl-piperazin-1-yl)-2-(tetrahydro-2H-pyran-4-ylamino)-benzamide, in particular wherein the composition comprising N-[5-(3,5-difluorobenzyl)-1H-indazol-3-yl]-4-(4-methyl-piperazin-1-yl)-2-(tetrahydro-2H-pyran-4-ylamino)-benzamide is as described in the present application, and a pH independent film coating wherein hydroxypropyl cellulose is incorporated into ethylcellulose.

In a further particular embodiment (Embodiment 49) the present invention provides a pharmaceutical composition comprising N-[5-(3,5-difluorobenzyl)-1H-indazol-3-yl]-4-(4-methyl-piperazin-1-yl)-2-(tetrahydro-2H-pyran-4-ylamino)-benzamide, in particular wherein the composition comprising N-[5-(3,5-difluorobenzyl)-1H-indazol-3-yl]-4-(4-methyl-piperazin-1-yl)-2-(tetrahydro-2H-pyran-4-ylamino)-benzamide is as described in the present application, and a film coating, in particular a pH independent film coating, comprising:

a) hydroxypropyl cellulose, and b) ethylcellulose.

In a further particular embodiment (Embodiment 50) the present invention provides a pharmaceutical composition comprising N-[5 -(3,5-difluorobenzyl)-1H-indazol-3 -yl]-4-(4-methyl-piperazin-1-yl)-2-(tetrahydro-2H-pyran-4-ylamino)-benzamide, in particular wherein the composition comprising N-[5-(3,5-difluorobenzyl)-1H-indazol-3-yl]-4-(4-methyl-piperazin-1-yl)-2-(tetrahydro-2H-pyran-4-ylamino)-benzamide is as described in the present application, and a film coating, in particular a pH independent film coating, comprising:

a) hydroxypropyl cellulose, b) ethylcellulose, and c) medium chain trigelcirides/caprilin and Caprin GB.

In a further particular embodiment (Embodiment 51) the present invention provides a pharmaceutical composition comprising N-[5-(3,5-difluorobenzyl)-1H-indazol-3-yl]-4-(4-methyl-piperazin-1-yl)-2-(tetrahydro-2H-pyran-4-ylamino)-benzamide, in particular wherein the composition comprising N-[5-(3,5-difluorobenzyl)-1H-indazol-3-yl]-4-(4-methyl-piperazin-1-yl)-2-(tetrahydro-2H-pyran-4-ylamino)-benzamide is as described in the present application, and a film coating, in particular a pH independent film coating, comprising:

a) hydroxypropyl cellulose, b) ethylcellulose, c) medium chain trigelcirides/caprilin and Caprin GB, and d) oleic acid In a further particular embodiment (Embodiment 52) the present invention provides a pharmaceutical composition comprising N-[5-(3,5-difluorobenzyl)-1H-indazol-3-yl]-4-(4-methyl-piperazin-1-yl)-2-(tetrahydro-2H-pyran-4-ylamino)-benzamide, in particular wherein the composition comprising N-[5-(3,5-difluorobenzyl)-1H-indazol-3-yl]-4-(4-methyl-piperazin-1-yl)-2-(tetrahydro-2H-pyran-4-ylamino)-benzamide is as described in the present application, and a film coating, in particular a pH independent film coating, comprising:

a) hydroxypropyl cellulose,
b) ethylcellulose,
c) medium chain trigelcirides/caprilin and Caprin GB,
d) oleic acid, and
e) Iron oxide red.

In a further particular embodiment (Embodiment 53) the present invention as described above wherein the film coating, in particular wherein the film coating is a pH independent film coating, comprises a) 1% to 8% by weight, in particular 2% to 8% by weight, more particularly 4.5% to 5.5% by weight of hydroxypropyl cellulose,
b) 60% to 90% by weight, in particular 65% to 80% by weight, more particularly 70% to 75% by weight of ethylcellulose,
c) 1% to 25% by weight, in particular 5% to 20% by weight, more particularly 12% to 16% by weight of medium chain trigelcirides/caprilin and Caprin GB,
d) 3% to 15% by weight, in particular 5% to 12% by weight, more particularly 7.5% to 9% by weight of oleic acid, and
e) 0.05% to 0.6% by weight, in particular 0.1% to 0.5% by weight, more particularly 0.2% to 0.4% by weight of Iron oxide red.

In particular embodiment (Embodiment 54) of the invention, the pharmaceutical composition comprises only one active pharmaceutical ingredient (API), more particularly wherein the only API is N-[5-(3,5-difluorobenzyl)-1H-indazol-3-yl]-4-(4-methyl-piperazin-1-yl)-2-(tetrahydro-2H-pyran-4-ylamino)-benzamide also known as entrectinib.

Figure 5:
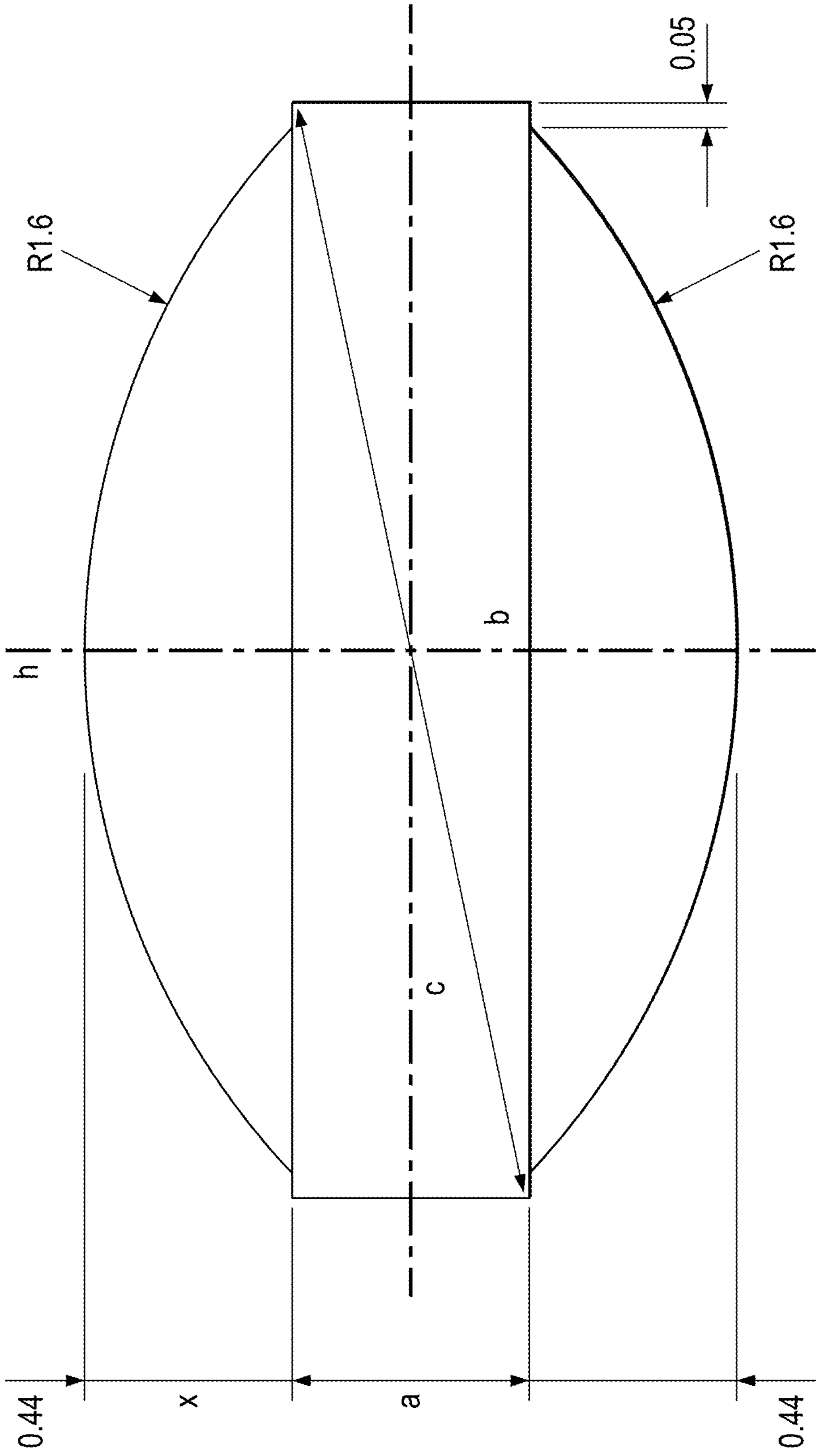
FIG. 5: Punch drawing to produce Minitablets of b:diameter=2.35±0.06 mm; h:tablet height=2.25±0.10 mm; a: base height=1.37±0.10 mm; x: cap height=0.44±0.02 mm; c: longest lengths=2.72±0.10 mm.

In yet another embodiment (Embodiment 55)according to any of the embodiment mentioned herein, the invention provides the pharmaceutical compositions as described according to any of the embodiments mentioned herein in the form of a minitablets. In particular embodiment the minitablets comprise intragranular components, extragranular components as defined herein and a film coating, more particularly wherein the minitablets comprise intragranular components, extragranular components as defined herein and a pH independent film coating as defined herein. In other particular embodiment, the minitablets have a shape as drawn in FIG. 5, more particularly the minitablets according to FIG. 5 have a tablet height (h) of 2.25±0.10 mm, particularly have also diameter (b) of 2.35±0.06 mm; more particularly have also a base height (a)=1.37±0.10 mm; even more particularly have also a cap height (x) of 0.44±0.02 mm; most particularly have a longest lengths (c) of 2.72±0.10 mm. In particular, the minitablets can be filled in capsules or in stickpacks. In more particular, the minitablets can be filled in stickpacks.

In particular embodiments (Embodiment 56) of the pharmaceutical composition as described according to any of the embodiments mentioned herein comprises from about 2.5 mg to about 100 mg of N-[5-(3,5-difluorobenzyl)-1H-indazol-3-yl]-4-(4-methyl-piperazin-1-yl)-2-(tetrahydro-pyran-4-ylamino)-benzamide.

In particular embodiments (Embodiment 57) of the pharmaceutical composition as described herein wherein pharmaceutical composition is in the form of minitablets having a diameter from 1.00 mm to 3.00 mm, more particularly 1.5 mm to 2.5 mm, most particularly 2.4 mm±0.2 mm.

In particular embodiments (Embodiment 58) of the pharmaceutical composition as described herein wherein pharmaceutical composition is in the form of minitablets having a diameter of 2.4±0.2 mm and height of 2.4±0.2 mm.

In particular embodiments (Embodiment 59) of the pharmaceutical composition as described herein wherein pharmaceutical composition is in the form of minitablets with individual dosage of 2.5 mg of entrectinib.

In yet another particular embodiments (Embodiment 60) the present invention provides minitablets having a diameter of 2.4±0.2 mm and height of 2.4±0.2 mm with a pharmaceutical composition as described according to any of the embodiment herein.

In yet another particular embodiments (Embodiment 61) the present invention provides a minitablet with a pharmaceutical composition according to any of the embodiments described herein, in particular with a dosage of 2.5 mg of entrectinib per minitablet.

In particular embodiments (Embodiment 62) of the pharmaceutical composition as described herein wherein pharmaceutical composition is in the form of minitablets and it is being administered with food, for example with yoghurt.

In particular embodiments (Embodiment 63) of the pharmaceutical composition as described herein wherein pharmaceutical composition is in the form of minitablets and wherein the mintablet are being sprinkle in food, for example in yoghurt, more particularly in a spoon of a yoghurt, even more particularly in about 15 ml of yoghurt.

In yet another particular embodiments (Embodiment 64) the present invention provides a stickpack comprising minitablets according to any of the embodiments described herein, in particular wherein the minitablets have a pharmaceutical composition according to any of the embodiments described herein, more particularly where the stickpack comprises between 5 and 100 minitablets, more particularly between 10 and 50 minitablets even more particularly 20 minitablets, most particularly wherein the minitablets have an individual dosage of 2.5 mg of entrectinib.

In yet another particular embodiments (Embodiment 65) the present invention provides a stickpack comprising minitablets according to any of the embodiments described herein, in particular wherein the minitablets have a pharmaceutical composition according to any of the embodiments described herein, more particularly where the stickpack comprises between 5 and 100 minitablets, more particularly between 10 and 50 minitablets even more particularly 20 minitablets, most particularly wherein the minitablets have an individual dosage of 2.5 mg of entrectinib.

In another embodiment (Embodiment 66) the invention provides a kit comprising a pharmaceutical composition as described therein in the form of a capsule, a tablet or a stickpack comprising a therapeutically effective amount of N-[5-(3,5-difluorobenzyl)-1H-indazol-3-yl]-4-(4-methyl-piperazin-1-yl)-2-(tetrahydro-pyran-4-ylamino)-benzamide, prescribing information also known as "leaflet", a blister package or bottle (HDPE or glass) and a container. The prescribing information preferably includes the advice to a patient regarding the administration of the N-[5-(3,5-difluorobenzyl)-1H-indazol-3-yl]-4-(4-methyl-piperazin-1-yl)-2-(tetrahydro-pyran-4-ylamino)-benzamide with food, more particularly within 30 minutes of breakfast.

In a further embodiment (Embodiment 67), the present invention relates to a process to produce the pharmaceutical composition as described herein, in particular a process comprising the following steps i) blend N-[5-(3,5-difluorobenzyl)-1H-indazol-3-yl]-4-(4-methyl-piperazin-1-yl)-2-(tetrahydro-2H-pyran-4-ylamino)-benzamide, also known as entrectinib, Colloidal Silicon Dioxide, Sodium stearyl fumarate, Croscarmellose Sodium, Microcrystalline cellulose and tartaric acid, in container 1;
ii) dry granulation, preferably roller compaction, of the mixture of container 1;
iii) sieve blend the mixture of Colloidal Silicon Dioxide, Mannitol, Magnesium stearate, and Croscarmellose Sodium having a screen size approximately of 0.8 mm for Colloidal Silicon Dioxide, Mannitol and croscarmellose and of 0.5 mm for Magnesium stearate into Container 2,
iv) granulate the mixture of container 1 with the mixture of Container 2,
v) the granules obtained in iv) are blend
vi) compress the blend of v) iv)into tablet kernels, and
vii) prepare the film-coating system:
  a) mixing Polyvinyl alcohol-part. Hydrolyzed, Titanium dioxide, Macrogol/PEG, (MW3350,Macrogol 4000 JP), Talc, Iron oxide yellow, Iron oxide red, Ferrosoferric oxide (NF)/Black iron oxide (JPE) into a film coating mixture,
  b) suspend the mixture into purified water, and
viii) spray the film coating system vii) onto the tablet kernels.

In a further embodiment (Embodiment 68), the present invention relates to a process to produce the pharmaceutical composition as described herein, in particular a process comprising the following steps
i) blend N-[5-(3,5-difluorobenzyl)-1H-indazol-3-yl]-4-(4-methyl-piperazin-1-yl)-2-(tetrahydro-2H-pyran-4-ylamino)-benzamide, also known as entrectinib, Colloidal Silicon Dioxide, Sodium stearyl fumarate, Croscarmellose Sodium, Microcrystalline cellulose and tartaric acid, in container 1;
ii) dry granulation, preferably roller compaction, of the mixture of container 1;
iii) sieve blend the mixture of Colloidal Silicon Dioxide, Mannitol, Magnesium stearate, and Croscarmellose Sodium having a screen size approximately of 0.8 mm for Colloidal Silicon Dioxide, Mannitol and croscarmellose and of 0.5 mm for Magnesium stearate into Container 2,
iv) granulate, particular dry granulation, the mixture of container 1 with the mixture of container 2,
v) the granules obtained in iv) are blend
vi) compress the blend of v) into tablet kernels, and
vii) prepare the film-coating system:
  a) mixing purified water and Iron oxide red and homogenize, in particular using a homogenizer Polytron,
  b) hydroxypropyl cellulose is suspended to the homogenize mixture of a), in particular using a propeller agitator,
  c) adding suspension of b) in particular using a paddle agitator to film coating dispersion which comprises Purified water, ethylcellulose 20 cP Ammonium Hydroxide 28%, Medium chain triglycerides/caprilin and Caprin GB, and Oleic acid;
viii) spray the film coating system vii) onto the tablet kernels.

In another particular embodiment (Embodiment 69), the present invention provides a pharmaceutical composition obtained by the process described herein.

In another embodiment (Embodiment 70), are provided pharmaceutical compositions as described in the above mentioned embodiment comprising N-[5-(3,5-difluorobenzyl)-1H-indazol-3-yl]-4-(4-methyl-piperazin-1-yl)-2-(tetrahydro-pyran-4-ylamino)-benzamide that can be administered to the mammal at any suitable dosage (e. g., to achieve a therapeutically effective amount). For example, a suitable dose of a therapeutically effective amount of 2.5 mg to 600 mg per day. In one aspect are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide for administration to a patient will be between approximately 2.5 mg to about 600 mg per day. A desirable dose is preferably about 50 mg to about 600 mg per day.

In yet another embodiment (Embodiment 71), the pharmaceutical compositions as described according to any of the embodiments mentioned herein are useful for the treatment of cancers comprising but not limited to cancers of the: circulatory system, for example, heart (sarcoma [angiosarcoma, fibrosarcoma, rhabdomyosarcoma, liposarcoma], myxoma, rhabdomyoma, fibroma, lipoma and teratoma), mediastinum and pleura, and other intrathoracic organs, vascular tumors and tumor-associated vascular tissue; respiratory tract, for example, nasal cavity and middle ear, accessory sinuses, larynx, trachea, bronchus and lung such as small cell lung cancer (SCLC), non-small cell lung cancer (NSCLC), bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; gastrointestinal system, for example, esophagus (squamous cell carcinoma, adenocarcinoma, leiomyosarcoma, lymphoma), stomach (carcinoma, lymphoma, leiomyosarcoma), gastric, pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); genitourinary tract, for example, kidney (adenocarcinoma, Wilm's tumor [nephroblastoma], lymphoma, leukemia), bladder and/or urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); liver, for example, hepatoma (hepatocellular carcinoma), cholangiocarcinoma, hepatoblastoma, angiosarcoma, hepatocellular adenoma, hemangioma, pancreatic endocrine tumors (such as pheochromocytoma, insulinoma, vasoactive intestinal peptide tumor, islet cell tumor and glucagonoma); bone, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; nervous system, for example, neoplasms of the central nervous system (CNS), primary CNS lymphoma, skull cancer (osteoma, hemangioma, granuloma, xanthoma, osteitis deformans), meninges (meningioma, meningiosarcoma, gliomatosis), brain cancer (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); reproductive system, for example, gynecological, uterus (endometrial carcinoma), cervix (cervical carcinoma, pretumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma) and other sites associated with female genital organs; placenta, penis, prostate, testis, and other sites associated with male genital organs; hematologic system, for example, blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; oral cavity, for example, lip, tongue, gum, floor of mouth, palate, and other parts of mouth, parotid gland, and other parts of the salivary glands, tonsil, oropharynx, nasopharynx, pyriform sinus, hypopharynx, and other sites in the lip, oral cavity and pharynx; skin, for example, malignant melanoma, cutaneous melanoma, basal cell carcinoma, squamous cell carcinoma, Karposi's sarcoma, moles dysplastic nevi, lipoma, angioma, dermatofibroma, and keloids; adrenal glands: neuroblastoma; and other tissues comprising connective and soft tissue, retroperitoneum and peritoneum, eye, intraocular melanoma, and adnexa, breast, head or/and neck, anal region, thyroid, parathyroid, adrenal gland and other endocrine glands and related structures, secondary and unspecified malignant neoplasm of lymph nodes, secondary malignant neoplasm of respiratory and digestive systems and secondary malignant neoplasm of other sites.

More specifically, examples of cancer when used herein in connection with pharmaceutical compositions as described according to any of the embodiments mentioned herein, include cancer selected from lung cancer (NSCLC and SCLC), cancer of the head or neck, ovarian cancer, colon cancer, rectal cancer, prostate cancer, cancer of the anal region, stomach cancer, breast cancer, cancer of the kidney or ureter, renal cell carcinoma, carcinoma of the renal pelvis, neoplasms of the central nervous system (CNS), primary CNS lymphoma, non-Hodgkins's lymphoma, spinal axis tumors, or a combination of one or more of the foregoing cancers.

In some more particular embodiments (Embodiment 72), the pharmaceutical compositions as described according to any of the embodiments mentioned herein are useful for the treatment of cancers, comprising Spitz melanoma, perineural invasion, pulmonary large cell neuroendocrine carcinoma, uterine carcinoma, juvenile breast cancer, nasopharyngeal carcinoma, adenoid cystic cancer, meduallary thyroid cancer, salivary cancer, congenital infantile fibrosarcoma, mesoblastic nephroma, esophageal cancer (squamous), diffuse large B-cell lymphoma, papillary thyroid cancer, and mammary analogue secretory carcinoma.

In some other embodiments (Embodiment 73), the invention provides methods for treating diseases caused by and/or associated with deregulated protein kinase activity, particularly PLK family, protein kinase C in different isoforms, Met, PAK-4, PAK-5, ZC-1, STLK-2, DDR-2, Aurora 1, Aurora 2, Bub-1, Chk1, Chk2, HER2, rafl, MEK1, MAPK, EGF-R, PDGF-R, FGF-R, FLT3, JAK2, IGF-R, ALK, PI3K, weel kinase, Src, Abl, Akt, MAPK, ILK, MK-2, IKK-2, Cdc7, Nek, Cdk/cyclin kinase family, more particularly Aurora 2, IGF-1R and ALK activity, and ROS1 activity, and further more particularly ALK activity and/or ROS1 activity, which comprises administering to a mammal in need thereof an effective amount of a pharmaceutical composition, as described according to any of the embodiments mentioned herein.

Other embodiment (Embodiment 74), discloses herein are directed to treat a disease caused by and/or associated with dysregulated protein kinase activity selected from the group consisting of cancer and cell proliferative disorders.

Particular embodiment (Embodiment 75) provides methods to treat specific types of cancer comprising carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xeroderma pigmentosum, angiosarcoma, glioblastoma, holangiocarcinoma, inflammatory myofibroblastic tumor, epitheloid hemangioendothelioma, astrocytoma, meningioma, angiosarcoma, epitheloid hemangiothelioma, keratocanthomas, thyroid follicular cancer, Kaposi's sarcoma, and pancreatic cancer.

Particular embodiment (Embodiment 76) discloses herein are directed to treating specific types of cancer such as, but not restricted to, breast cancer, lung cancer, colorectal cancer, prostate cancer, ovarian cancer, endometrial cancer, gastric cancer, clear cell renal cell carcinoma, invasive ductal carcinoma (breast), uveal melanoma, multiple myeloma, rhabdomyosarcoma, Ewing's sarcoma, Kaposi's sarcoma, pancreatic cancer, and medulloblastoma.

Particular embodiment (Embodiment 77) provides methods of treating ALK+ Anaplastic Large Cell Lymphomas (ALCL) and possibly other indications in which the ALK activity might play a role, like Neuroblastoma, Rhabdomyosarcoma, Glioblastoma, Inflammatory Myofibroblastic Tumor, and some kind of Melanomas, Breast Carcinomas, Ewings sarcomas, Retinoblastomas and Non-Small Cell Lung Carcinomas (NSCLC).

Particular embodiment (Embodiment 78) provides methods to treat, reduce the symptoms of, ameliorate the symptoms of, delay the onset of, or otherwise pharmaceutically address pancreatic cancer and possibly other indications in which a defect in the modulation of ROS1 activity, or upregulation, misregulation or deletion thereof might play a role by administering a pharmaceutical composition, as described according to any of the embodiments mentioned herein. Particular embodiment (Embodiment 79) provides methods to treat, reduce the symptoms of, ameliorate the symptoms of, delay the onset of, or otherwise pharmaceutically address pancreatic cancer and possibly other indications in which a defect in the modulation of ROS1 activity, or upregulation, misregulation or deletion thereof might play a role by administering a by administering a pharmaceutical compositions as described according to any of the embodiments mentioned herein. In some embodiments are provided methods to treat, reduce the symptoms of, ameliorate the symptoms of, delay the onset of, or otherwise pharmaceutically address pancreatic cancer and possibly other indications in which a defect in the modulation of ROS1 activity, or upregulation, misregulation or deletion thereof might play a role by administering a pharmaceutical composition as provided herein.

Particular embodiment (Embodiment 80) provides methods to treat, reduce the symptoms of, ameliorate the symptoms of, delay the onset of, or otherwise pharmaceutically address pancreatic cancer and possibly other indications in which a defect in the modulation of ALK, ROS1, TrkA, TrkB, or TrkC activity, or a combination thereof, or upregulation, misregulation or deletion thereof might play a role by administering a pharmaceutical composition as provided herein. In some embodiments are provided methods to treat, reduce the symptoms of, ameliorate the symptoms of, delay the onset of, or otherwise pharmaceutically address pancreatic cancer and possibly other indications in which a defect in the modulation of ALK, ROS1, TrkA, TrkB, or TrkC activity, or a combination thereof, or upregulation, misregulation or deletion thereof might play a role by administering a pharmaceutical composition as provided herein.

Particular embodiment (Embodiment 81) provides methods to treat, reduce the symptoms of, ameliorate the symptoms of, delay the onset of, or otherwise pharmaceutically address pancreatic cancer and possibly other indications in which a defect in the modulation of ROS1 activity, or upregulation, misregulation or deletion thereof might play a role by administering a pharmaceutical composition as provided herein. In some embodiments are provided methods to treat, reduce the symptoms of, ameliorate the symptoms of, delay the onset of, or otherwise pharmaceutically address pancreatic cancer and possibly other indications in which a defect in the modulation of ROS1 activity, or upregulation, misregulation or deletion thereof might play a role by administering a pharmaceutical composition as provided herein. In some embodiments are provided methods to treat, reduce the symptoms of, ameliorate the symptoms of, delay the onset of, or otherwise pharmaceutically address pancreatic cancer and possibly other indications in which a defect in the modulation of ROS1 activity, or upregulation, misregulation or deletion thereof might play a role by administering a pharmaceutical composition as provided herein.

Particular embodiment (Embodiment 82) provides methods to treat, reduce the symptoms of, ameliorate the symptoms of, delay the onset of, or otherwise pharmaceutically address pancreatic cancer and possibly other indications in which a defect in the modulation of ALK, ROS1, TrkA, TrkB, or TrkC activity, or a combination thereof, or upregulation, misregulation or deletion thereof might play a role by administering pharmaceutical composition as provided herein. In some embodiments are provided methods to treat, reduce the symptoms of, ameliorate the symptoms of, delay the onset of, or otherwise pharmaceutically address pancreatic cancer and possibly other indications in which a defect in the modulation of ROS1, TrkA, TrkB, or TrkC activity, or a combination thereof, activity, or upregulation, misregulation or deletion thereof might play a role by administering a pharmaceutical composition as provided herein.

Particular embodiment (Embodiment 83) provides methods to treat, reduce the symptoms of, ameliorate the symptoms of, delay the onset of, or otherwise pharmaceutically address pancreatic cancer and possibly other indications in which a defect in the modulation of ROS1, TrkA, TrkB, or TrkC activity, or a combination thereof, activity, or upregulation, misregulation or deletion thereof might play a role by administering a pharmaceutical composition as provided herein. In some embodiments are provided methods to treat, reduce the symptoms of, ameliorate the symptoms of, delay the onset of, or otherwise pharmaceutically address pancreatic cancer and possibly other indications in which a defect in the modulation of ROS1, TrkA, TrkB, or TrkC activity, or a combination thereof, activity, or upregulation, misregulation or deletion thereof might play a role by administering a pharmaceutical composition as provided herein. In some embodiments are provided methods to treat, reduce the symptoms of, ameliorate the symptoms of, delay the onset of, or otherwise pharmaceutically address pancreatic cancer and possibly other indications in which a defect in the modulation of ROS1, TrkA, TrkB, or TrkC activity, or a combination thereof, activity, or upregulation, misregulation or deletion thereof might play a role by administering a pharmaceutical composition as provided herein.

Particular embodiment (Embodiment 84) are provides methods to treat, reduce the symptoms of, ameliorate the symptoms of, delay the onset of, or otherwise pharmaceutically address pancreatic cancer associated with a ROS1 down-regulation defect, for example a null mutation such as a ROS1 deletion by identifying a ROS1 down-regulation defect, for example a null mutation such as a ROS1 deletion in a cancer or precancerous pancreatic cell in an subject, and administering to the subject a pharmaceutical composition as provided herein. In some embodiments are provided methods to treat, reduce the symptoms of, ameliorate the symptoms of, delay the onset of, or otherwise pharmaceutically address pancreatic cancer associated with a ROS1 down-regulation defect, for example a null mutation such as a ROS1 deletion by identifying a ROS1 down-regulation defect, for example a null mutation such as a ROS1 deletion in a cancer or precancerous pancreatic cell in an subject, and administering to the subject a pharmaceutical composition as provided herein. In some embodiments are provided methods to treat, reduce the symptoms of, ameliorate the symptoms of, delay the onset of, or otherwise pharmaceutically address pancreatic cancer associated with a ROS1 down-regulation defect, for example a null mutation such as a ROS1 deletion by identifying a ROS1 down-regulation defect, for example a null mutation such as a ROS1 deletion in a cancer or precancerous pancreatic cell in an subject, and administering to the subject a pharmaceutical composition as provided herein.

Particular embodiment (Embodiment 85) provides methods to treat, reduce the symptoms of, ameliorate the symptoms of, delay the onset of, or otherwise pharmaceutically address pancreatic cancer associated with a ALK, ROS1, TrkA, TrkB, or TrkC down-regulation defect, for example a null mutation such as a ALK, ROS1, TrkA, TrkB, or TrkC deletion by identifying a ALK, ROS1, TrkA, TrkB, or TrkC down-regulation defect, for example a null mutation such as a ALK, ROS1, TrkA, TrkB, or TrkC deletion in a cancer or precancerous pancreatic cell in an subject, and administering to the subject a pharmaceutical composition as provided herein.

Particular embodiment (Embodiment 86) provides methods to treat, reduce the symptoms of, ameliorate the symptoms of, delay the onset of, or otherwise pharmaceutically address a condition selected from non-small cell lung cancer, papillary thyroid cancer, neuroblastoma, pancreatic cancer and colorectal cancer and possibly other indications in which a defect in the modulation of ALK, ROS1, TrkA, TrkB, or TrkC activity, or a combination thereof, or upregulation, misregulation or deletion thereof might play a role by administering pharmaceutical composition as provided herein. In some embodiments are provided methods to treat, reduce the symptoms of, ameliorate the symptoms of, delay the onset of, or otherwise pharmaceutically address pancreatic cancer and possibly other indications in which a defect in the modulation of ROS1, TrkA, TrkB, or TrkC activity, or a combination thereof, activity, or upregulation, misregulation or deletion thereof might play a role by administering a pharmaceutical composition as provided herein.

Particular embodiment (Embodiment 87) provides methods to treat, reduce the symptoms of, ameliorate the symptoms of, delay the onset of, or otherwise pharmaceutically address a condition selected from non-small cell lung cancer, papillary thyroid cancer, neuroblastoma, pancreatic cancer and colorectal cancer and possibly other indications in which a defect in the modulation of ROS1, TrkA, TrkB, or TrkC activity, or a combination thereof, activity, or upregulation, misregulation or deletion thereof might play a role by administering a pharmaceutical composition as provided herein. In some embodiments are provided methods to treat, reduce the symptoms of, ameliorate the symptoms of, delay the onset of, or otherwise pharmaceutically address a condition selected from non-small cell lung cancer, papillary thyroid cancer, neuroblastoma, pancreatic cancer and colorectal cancer and possibly other indications in which a defect in the modulation of ROS1, TrkA, TrkB, or TrkC activity, or a combination thereof, activity, or upregulation, misregulation or deletion thereof might play a role by administering a pharmaceutical composition as provided herein. In some embodiments are provided methods to treat, reduce the symptoms of, ameliorate the symptoms of, delay the onset of, or otherwise pharmaceutically address a condition selected from non-small cell lung cancer, papillary thyroid cancer, neuroblastoma, pancreatic cancer and colorectal cancer and possibly other indications in which a defect in the modulation of ROS1, TrkA, TrkB, or TrkC activity, or a combination thereof, activity, or upregulation, misregulation or deletion thereof might play a role by administering a pharmaceutical composition as provided herein.

Particular embodiment (Embodiment 88) provides methods to treat, reduce the symptoms of, ameliorate the symptoms of, delay the onset of, or otherwise pharmaceutically address a condition selected from non-small cell lung cancer, papillary thyroid cancer, neuroblastoma, pancreatic cancer and colorectal cancer associated with a ROS1 down-regulation defect, for example a null mutation such as a ROS1 deletion by identifying a ROS1 down-regulation defect, for example a null mutation such as a ROS1 deletion in a cancer or precancerous cell in a subject, and administering to the subject a pharmaceutical composition as provided herein. In some embodiments are provided methods to treat, reduce the symptoms of, ameliorate the symptoms of, delay the onset of, or otherwise pharmaceutically address a condition selected from non-small cell lung cancer, papillary thyroid cancer, neuroblastoma, pancreatic cancer and colorectal cancer associated with a ROS1 down-regulation defect, for example a null mutation such as a ROS1 deletion by identifying a ROS1 down-regulation defect, for example a null mutation such as a ROS1 deletion in a cancer or precancerous cell in a subject, and administering to the subject a pharmaceutical composition as provided herein. In some embodiments are provided methods to treat, reduce the symptoms of, ameliorate the symptoms of, delay the onset of, or otherwise pharmaceutically address a condition selected from non-small cell lung cancer, papillary thyroid cancer, neuroblastoma, pancreatic cancer and colorectal cancer associated with a ROS1 down-regulation defect, for example a null mutation such as a ROS1 deletion by identifying a ROS1 down-regulation defect, for example a null mutation such as a ROS1 deletion in a cancer or precancerous cell in a subject, and administering to the subject a pharmaceutical composition as provided herein.

Particular embodiment (Embodiment 89) provides methods to treat, reduce the symptoms of, ameliorate the symptoms of, delay the onset of, or otherwise pharmaceutically address a condition selected from non-small cell lung cancer, papillary thyroid cancer, neuroblastoma, pancreatic cancer and colorectal cancer associated with a ALK, ROS1, TrkA, TrkB, or TrkC down-regulation defect, for example a null mutation such as a ALK, ROS1, TrkA, TrkB, or TrkC deletion by identifying a ALK, ROS1, TrkA, TrkB, or TrkC down-regulation defect, for example a null mutation such as a ALK, ROS1, TrkA, TrkB, or TrkC deletion in a cancer or precancerous cell in a subject, and administering to the subject a pharmaceutical composition as provided herein.

Particular embodiment (Embodiment 90) provides methods of treating cancer in a subject in need thereof, the method comprising inhibiting ALK, ROS1, TrkA, TrkB, or TrkC activity, or a combination thereof, in said subject, by administering to said subject a pharmaceutical composition as provided herein that comprises an effective amount of N-[5-(3,5-difluorobenzyl)-1H-indazol-3-yl]-4-(4-methyl-piperazin-1-yl)-2-(tetrahydro-2H-pyran-4-ylamino)-benzamide.

Particular embodiment (Embodiment 91) provides methods of treating non-small cell lung cancer, papillary thyroid cancer, neuroblastoma, pancreatic cancer or colorectal cancer in a subject, comprising administering to said subject a pharmaceutical composition as provided herein that comprises an effective amount of N-[5-(3,5-difluorobenzyl)-1H-indazol-3-yl]-4-(4-methyl-piperazin-1-yl)-2-(tetrahydro-2H-pyran-4-ylamino)-benzamide.

Particular embodiment (Embodiment 92) provides methods of treating tumors in a subject, said methods comprising administering to the subject a pharmaceutical composition as provided herein that comprises an effective amount of N-[5-(3,5-difluorobenzyl)-1H-indazol-3-yl]-4-(4-methyl-piperazin-1-yl)-2-(tetrahydro-2H-pyran-4-ylamino)-benzamide.

Particular embodiment (Embodiment 93) provides any of the methods described herein wherein the subject or subject is suffering from cancer and the cancer is selected from at least one of non-small cell lung cancer, papillary thyroid cancer, neuroblastoma, pancreatic cancer and colorectal cancer. Some embodiments provide any of the methods described herein wherein the subject or subject is suffering from non-small cell lung cancer. Some embodiments provide any of the methods described herein wherein the subject or subject is suffering from papillary thyroid cancer. Some embodiments provide any of the methods described herein wherein the subject or subject is suffering from neuroblastoma. Some embodiments provide any of the methods described herein wherein the subject or subject is suffering from pancreatic cancer. Some embodiments provide any of the methods described herein wherein the subject or subject is suffering from colorectal cancer.

In some instances of the methods provided herein, the cancer is selected from the group consisting of anaplastic large-cell lymphoma (ALCL), colorectal cancer (CRC), cholangiocarcinoma, gastric, glioblastomas (GBM), leiomyosarcoma, melanoma, non-small cell lung cancer (NSCLC), squamous cell lung cancer, neuroblastoma (NB), ovarian cancer, pancreatic cancer, prostate cancer, medullary thyroid cancer, breast cancer, and papillary thyroid cancer.

Particular embodiment (Embodiment 94) relates to any of the pharmaceutical compositions, as described according to any of the embodiments mentioned herein, for use as a medicament. Some embodiments relate to the use of any of the pharmaceutical compositions provided herein for the manufacture of a medicament for the treatment of abnormal cell growth.

In some embodiments are provided pharmaceutical compositions as described according to any of the herein embodiments comprising N-[5-(3,5-difluorobenzyl)-1H-indazol-3-yl]-4-(4-methyl-piperazin-1-yl)-2-(tetrahydropyran-4-ylamino)-benzamide, wherein said pharmaceutical composition when administered to a subject in a fasted or fed state at a total dose of about 300 $mg/m^2$ of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the $T_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 2 hours and about 5 hours, or between about 2.5 hours and about 4.7 hours, or between about 2.4 hours and about 4.7 hours, or between about 2.6 hours and about 4.8 hours, following said administration of said pharmaceutical composition to said subject.

In particular embodiment (Embodiment 95), the invention provides a method of treating a subject having cancer, the method comprising administering to the subject the pharmaceutical composition as herein described.

In another embodiment (Embodiment 96), the invention provides a method of treating a subject having ALK, ROS1, TrkA, TrkB, or TrkC positive cancer, or a combination thereof, the method comprising administering to the subject the pharmaceutical composition as herein described.

In another embodiment (Embodiment 97), the invention provides a method of treating a subject having ALK positive cancer, the method comprising administering to the subject the pharmaceutical composition as herein described.

In another embodiment (Embodiment 98), the invention provides a subject having ROS1, TrkA, TrkB, or TrkC positive cancer, or a combination thereof, the method comprising administering to the subject the pharmaceutical composition as herein described.

In another embodiment, the invention provides a method of treating a subject having ROS1 positive cancer, the method comprising administering to the subject the pharmaceutical composition as herein described.

In another embodiment (Embodiment 99), the invention provides a method of treating a subject having TrkA, TrkB, or TrkC positive cancer, or a combination thereof, the method comprising administering to the subject the pharmaceutical composition as herein described. In another embodiment, the invention provides a method of treating a subject having TrkA positive cancer, the method comprising administering to the subject the pharmaceutical composition as herein described.

In another embodiment (Embodiment 100), the invention provides a method of treating a subject having TrkB positive cancer, the method comprising administering to the subject the pharmaceutical composition as herein described.

In another embodiment(Embodiment 101), the invention provides a method of treating a subject having TrkC positive cancer, the method comprising administering to the subject the pharmaceutical composition as herein described.

[In another embodiment (Embodiment 102), the invention provides a pharmaceutical composition as herein described for use in a method of treating a subject having cancer.

In another embodiment(Embodiment 103), the invention provides a pharmaceutical composition as herein described for use in a method of treating a subject having ALK, ROS1, TrkA, TrkB, or TrkC positive cancer, or a combination thereof.

In another embodiment (Embodiment 104), the invention provides a pharmaceutical composition as herein described for use in a method of treating a subject having ALK positive cancer.

In another embodiment (Embodiment 105), the invention provides a pharmaceutical composition as herein described for use in a method of treating a subject having ROS1, TrkA, TrkB, or TrkC positive cancer, or a combination thereof.

In another embodiment (Embodiment 106), the invention provides a pharmaceutical composition as herein described for use in a method of treating a subject having ROS1 positive cancer.

In another embodiment (Embodiment 107), the invention provides a pharmaceutical composition as herein described for use in a method of treating a subject having TrkA, TrkB, or TrkC positive cancer, or a combination thereof.

In another embodiment (Embodiment 108), the invention provides a pharmaceutical composition as herein described for use in a method of treating a subject having TrkA positive cancer.

In another embodiment (Embodiment 109), the invention provides a pharmaceutical composition as herein described for use in a method of treating a subject having TrkB positive cancer.

In another embodiment (Embodiment 110), the invention provides a pharmaceutical composition as herein described for use in a method of treating a subject having TrkC positive cancer.

In another embodiment (Embodiment 111), the invention provides a use of the pharmaceutical composition as herein described for the preparation of a medicament for the treatment of cancer.

In another embodiment (Embodiment 112), the invention provides a use of the pharmaceutical composition as herein described for the preparation of a medicament for the treatment of ALK, ROS1, TrkA, TrkB, or TrkC positive cancer, or a combination thereof In another embodiment (Embodiment 113), the invention provides a use of the pharmaceutical composition as herein described for the preparation of a medicament for the treatment of ALK positive cancer.

In another embodiment (Embodiment 114), the invention provides a use of the pharmaceutical composition as herein described for the preparation of a medicament for the treatment of ROS1, TrkA, TrkB, or TrkC positive cancer, or a combination thereof.

In another embodiment (Embodiment 115), the invention provides a use of the pharmaceutical composition as herein described for the preparation of a medicament for the treatment of ROS1 positive cancer.

In another embodiment (Embodiment 116), the invention provides a use of the pharmaceutical composition as herein described for the preparation of a medicament for the treatment of TrkA, TrkB, or TrkC positive cancer, or a combination thereof.

In another embodiment (Embodiment 117), the invention provides a use of the pharmaceutical composition as herein described for the preparation of a medicament for the treatment of TrkA positive cancer.

In another embodiment (Embodiment 118), the invention provides a use of the pharmaceutical composition as herein described for the preparation of a medicament for the treatment of TrkB positive cancer.

In another embodiment (Embodiment 119), the invention provides a use of the pharmaceutical composition as herein described for the preparation of a medicament for the treatment of TrkC positive cancer.

Other features and embodiments of the invention will become apparent from the following examples which are given for illustration of the invention rather than for limiting its intended scope.

EXAMPLES

Example 1: Formulation A

A pharmaceutical composition comprising N-[5-(3,5-difluorobenzyl)-1H-indazol-3-yl]-4-(4-methyl-piperazin-1-yl)-2-(tetrahydro-2H-pyran-4-ylamino)-benzamide was prepared as follows.

TABLE 1

Composition of Formulation A

| Component | Target amount per dosage unit (mg) | % w/w of Total Weight | % w/w of Tablet core weight |
|---|---|---|---|
| Tablet core | | | |
| N-[5-(3,5-difluorobenzyl)-1H-indazol-3-yl]-4-(4-methyl-piperazin-1-yl)-2-(tetrahydro-2H-pyran-4-ylamino)-benzamide (form A) | 50.000 | 24.04% | 25.00% |
| Microcrystalline Cellulose | 95.000 | 45.67% | 47.50% |
| L-Tartaric acid (powder) | 14.740 | 7.09% | 7.37% |
| Colloidal Silicon Dioxide | 2.260 | 1.09% | 1.13% |
| Croscarmelose Sodium | 13.500 | 6.49% | 6.75% |
| Sodium stearyl fumarate | 3.600 | 1.73% | 1.80% |
| Mannitol | 20.000 | 9.62% | 10.00% |
| Magnesium stearate | 0.900 | 0.43% | 0.45% |
| Subtotal Weight (tablet core) | 200.000 | % w/w Film Coat Weight | |
| Film Coat: | | | |
| Film-Coating Mixture[a] Polyvinyl alcohol-part. Hydrolyzed | 3.200 | 1.54% | 40.00% |
| Titanium dioxide | 1.662 | 0.80% | 20.78% |
| Macrogol/PEG (MW3350, Macrogol 4000 JP) | 1.616 | 0.78% | 20.20% |
| Talc | 1.184 | 0.57% | 14.80% |
| Iron oxide yellow | 0.264 | 0.13% | 3.30% |
| Iron oxide red | 0.064 | 0.03% | 0.80% |
| Ferrosoferric oxide (NF)/Black iron oxide (JPE) | 0.010 | 0.005% | 0.12% |
| Purified water | N/A | N/A | N/A |
| Subtotal Weight (film coat) | 8.000 | | |
| Total Weight | 208.000 | | |

[a]A commercially available film-coating mixture by Colocom (e.g., Opadry) may be used.
b Purified water is used for aqueous film coating; it is essentially removed during processing.

A 8 kg batch was produced. The API, cellulose, tartaric acid, colloidal silica (part 1) and croscarmelose Sodium (part 1) are weighed and transferred in a suitable metaldrum of 20 l and mixed for 3 min at a speed of 20 upm. The mixture is then put through a 0.8 mm sieve manually in a 501 container. This is followed by an additional blending step for 5 min at 15 upm. Blend-screen-blend process is necessary to ensure absence of agglomerates. Particularly important for compression of small tablets.

Sodium stearyl fumarate is manually sieved through a 0.5 mm sieve and added to the powder mixture. This is then blended for 5 min at 15 upm.

Then, dry granulation using a roller compactor, was carried out. Particle size is increased and flow properties improved. The yield of the granulation was blended in a 201 metal drum for 1 min at 20 upm. The mannitol, croscarmellose sodium (part 2) and colloidal silica (part 2) were screened manually with a 0.8 mm screen and added to the granulate following by blending in a metal drum for 3 min at 20 upm. Theses excipients contribute to stable compression process as well as rapid disintegration of the tablets. Magnesium stearate is then manually screening using a 0.5 mm screen and added to the granulate followed by a blending step in the metal drum for 3 min at 20 upm. Tableting is carried out using multi-tip mini-tablet tooling on a standard manufacturing tablet machine (FETTE).

For both Formulation A and B, the same steps comprising from blending until tableting, are the same. The kernels are then differently coated in a Fluid Bed dryer using Wurster setup in a 1 kg Batch size. For Formulation A, the coating suspension was prepared by suspending the mix in purified water for at least 60 min in a 1 l steel beaker with a propeller stirrer at a speed of 450 upm. Prior to starting the process, the suspension was passed through a sieve (0.5 mm). During the coating process, the suspension was stirred with a blade agitator at a speed of 75 upm.

Example 2: Formulation B

A pharmaceutical composition comprising N-[5-(3,5-difluorobenzyl)-1H-indazol-3-yl]-4-(4-methyl-piperazin-1-yl)-2-(tetrahydro-2H-pyran-4-ylamino)-benzamide was prepared as follows.

TABLE 2

Composition of Formulation B

| Component | Target amount per dosage unit (mg) | % w/w of Total Weight | % w/w of Tablet core weight |
|---|---|---|---|
| Tablet core | | | |
| N-[5-(3,5-difluorobenzyl)-1H-indazol-3-yl]-4-(4-methyl-piperazin-1-yl)-2-(tetrahydro-2H-pyran-4-ylamino)-benzamide (form A) | 50.000 | 23.36% | 25.00% |
| Microcrystalline Cellulose | 95.000 | 44.39% | 47.50% |
| L-Tartaric acid (powder) | 14.740 | 6.89% | 7.37% |
| Colloidal Silicon Dioxide | 2.260 | 1.06% | 1.13% |
| Croscarmellose Sodium | 13.500 | 6.31% | 6.75% |
| Sodium stearyl fumarate | 3.600 | 1.68% | 1.80% |
| Mannitol | 20.000 | 9.35% | 10.00% |
| Magnesium stearate | 0.900 | 0.42% | 0.45% |
| Subtotal Weight (tablet core) | 200.000 | % w/w of Film Coat Weight | |
| Film Coat: | | | |
| Film-Coating Dispersion[a]: Purified water[b] | N/A | N/A | N/A |
| Ethylcellulose 20 cP | 9.970 | 4.66% | 71.21% |
| Ammonium Hydroxide 28%[b] | N/A | N/A | N/A |
| Medium chain triglycerides/Caprilin and Caprin GB | 2.121 | 0.99% | 15.15% |
| Oleic acid | 1.167 | 0.55% | 8.34% |
| Hydroxypropylcellulose | 0.700 | 0.33% | 5.00% |
| Iron oxide red | 0.042 | 0.02% | 0.30% |
| Purified water[c] | N/A | N/A | N/A |
| Subtotal Weight (film coat) | 14.000 | | |
| Total Weight | 214.000 | | |

[a]A commercially available 25% aqueous dispersion was used (e.g. Surelease).

[b]Essentially removed during processing.

[c]Purified water is used for aqueous film coating; it is essentially removed during processing.

The tablet core was produced according to example 1. The coating was made as follows. The iron oxide was homogenized in purified water using a homogenizer at 5000 upm for at least 15 min. Then the homogenizer is replaced by a lab-stirrer and the HPC was added while stirring with 430 upm for at least 60 min (Suspension part A). The commercially available coating suspension is prepared in a different steel beaker and stirred slowly. Then the suspension part A is added to the commerically available coating suspension while stirring at a speed of 50 upm. The resulting coating suspension is passed through a 0.5 mm sieve prior to the start of the coating process. During the process it is stirred at 50 upm.

Example 3: Formulation C

A pharmaceutical composition comprising N-[5-(3,5-difluorobenzyl)-1H-indazol-3-yl]-4-(4-methyl-piperazin-1-yl)-2-(tetrahydro-2H-pyran-4-ylamino)-benzamide was prepared as follows.

TABLE 3

| Composition of Formulation C | | |
|---|---|---|
| Component | Target amount per dosage unit (mg) | % w/w of Tablet core weight |
| Tablet core N-[5-(3,5-difluorobenzyl)-1H-indazol-3-yl]-4-(4-methyl-piperazin-1-yl)-2-(tetrahydro-2H-pyran-4-ylamino)-benzamide (form A) | 60.00 | 30.00 |
| Microcrystalline Cellulose | 99.80 | 49.90 |
| L-Tartaric acid (powder) | 17.70 | 8.85 |
| Colloidal Silicon Dioxide | 2.50 | 1.25 |
| Croscarmellose Sodium | 15.00 | 7.50 |
| Sodium stearyl fumarate | 5.00 | 2.50 |
| Subtotal Weight (tablet core) | 200.000 | 100.00 |
| Total Weight | 200.000 | 100.00 |

Formulation C was prepared on lab scale (~60g). Entrectinib, microcrystalline Cellulose, tartaric acid, colloidal silica (part 1) and croscarmellose sodium (part 1) were blended in a 0.4 l container for 3 min. This was followed by a sieving step through a 0.9 mm sieve. A second blending step followed the sieving (3min). Then Sodium stearyl fumarate was passed through a 0.5 mm sieve with subsequent blending of 5 min. Then roller compaction was simulated by carrying our slugging experiments. There already, sticking was observed. After compaction of slugs, they were milled using a conidur 0.8 mm sieve. The croscarmellose sodium (part 2) and the colloidal silica (part 2) was passed through 0.5 mm sieve and added

Example 4: Formulation D

The present example was made in accordance with the preparation of the composition of the Tablet core of example 1 wherein N-[5-(3,5-difluorobenzyl)-1H-indazol-3-yl]-4-(4-methyl-piperazin-1-yl)-2-(tetrahydro-2H-pyran-4-ylamino)-benzamide Form A is substituted by Form C. The composition of formulation is shown table 4.

TABLE 4

| Composition of Formulation D | | |
|---|---|---|
| Component | Target amount per dosage unit (mg) | % w/w of Tablet core weight |
| N-[5-(3,5-difluorobenzyl)-1H-indazol-3-yl]-4-(4-methyl-piperazin-1-yl)-2-(tetrahydro-2H-pyran-4-ylamino)-benzamide (form C) | 50.000 | 25.00% |
| Microcrystalline Cellulose | 95.000 | 47.50% |
| L-Tartaric acid (powder) | 14.740 | 7.37% |
| Colloidal Silicon Dioxide | 2.260 | 1.13% |
| Croscarmellose Sodium | 13.500 | 6.75% |
| Sodium stearyl fumarate | 3.600 | 1.80% |
| Mannitol | 20.000 | 10.00% |
| Magnesium stearate | 0.900 | 0.45% |

Example 5: Formulation E

Formulation E is a formulation containing no acidulant. The composition of formulation E is shown table 5. Formulation E can be made according to WO2019018570.

TABLE 5

| Composition of Formulation E | | | |
|---|---|---|---|
| | Amount (mg) | | |
| Component | 50 mg | 100 mg | 200 mg |
| Entrectinib | 50.00 | 100.00 | 200.00 |
| Mannitol, USP | 42.50 | 85.00 | 170.00 |
| Pre-gelatinized Starch, USP-NF | 17.13 | 34.25 | 68.50 |
| Colloidal Silecon Dioxide, USP-NF | 1.75 | 3.50 | 7.00 |
| Magnesium Stearate, USP-NF | 1.13 | 2.25 | 4.50 |
| Total fill wt. | 112.50 | 225.00 | 450.00 |
| Gelatin Capsule Shell | #4, opaque white | #2, opaque white | #0 opaque white |

Example 6: Formulation F

Formulation F is an amorphous formulation that was originally designed for pediatric patients. The composition of formulation F is shown table 6. Formulation F can be made according to WO2019077506.

TABLE 6

| Composition of Formulation F | |
|---|---|
| Component | Target amount per dosage unit (mg) |
| N-[5-(3,5-difluorobenzyl)-1H-indazol-3-yl]-4-(4-methyl-piperazin-1-yl)-2-(tetrahydro-2H-pyran-4-ylamino)-benzamide (form A) | 100.00 |
| Copovidon (Kollidon VA 64) | 25.00 mg |
| Microcrystalline Cellulose (Celphere CP-102) | 125.00 |

Formulation F was proven to not be stable.

By infrared assessment of hydrogen bonding, there was no evidence for extra stabilisation through hydrogen bonding interactions in the amorphous dispersion. In addition to the formulation mentioned in table 6 which represents entrectinib with copovidone at 80% drug load, an additional amorphous mixture entrectinib and copovidone at 90% drug load. AFM: Homogenous amorphous mixtures of the API were obtained with Copovidone at 80% and 90% drug loads.

Figure 6:
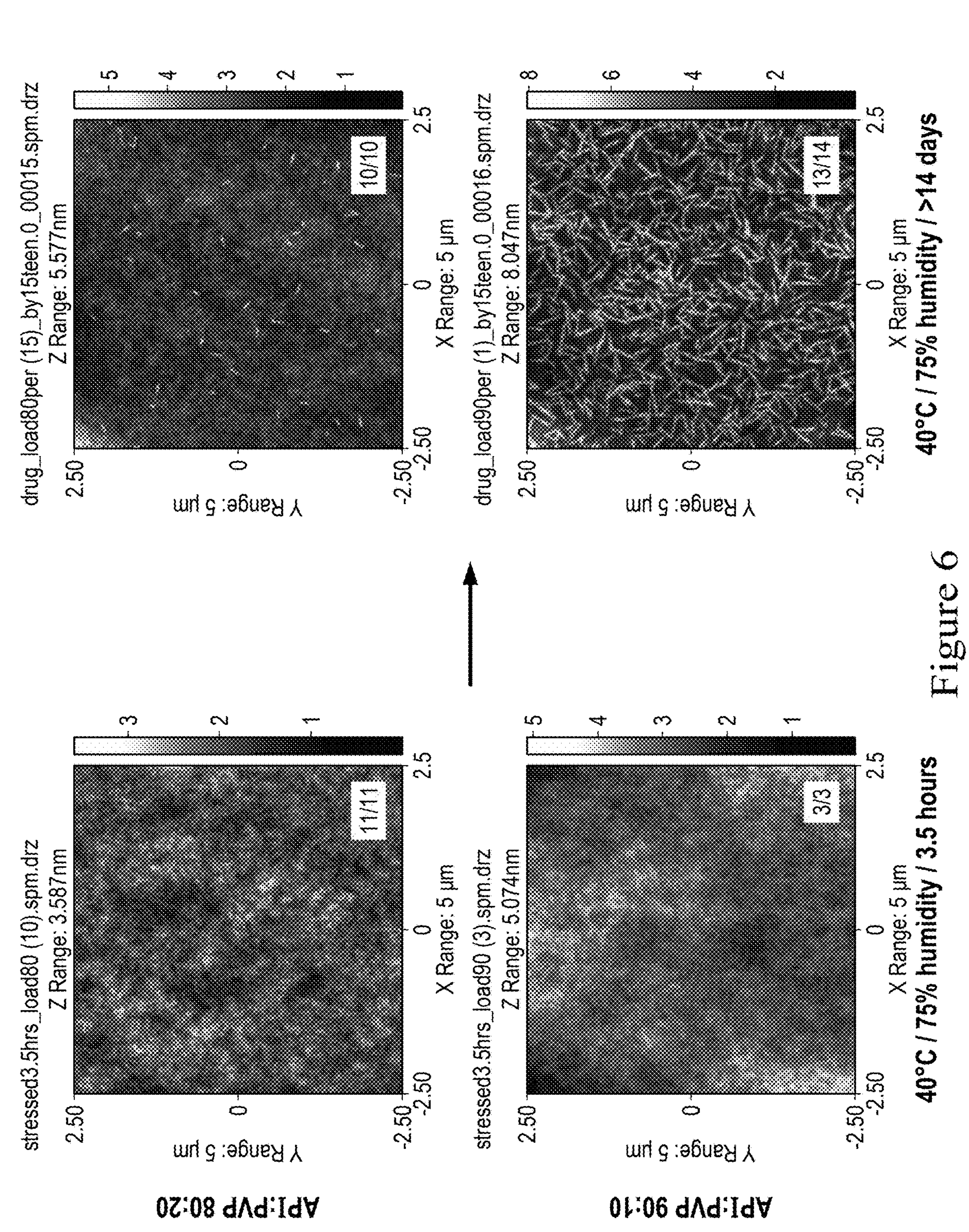
FIG. 6: Stability of formulation F
Figure 7:
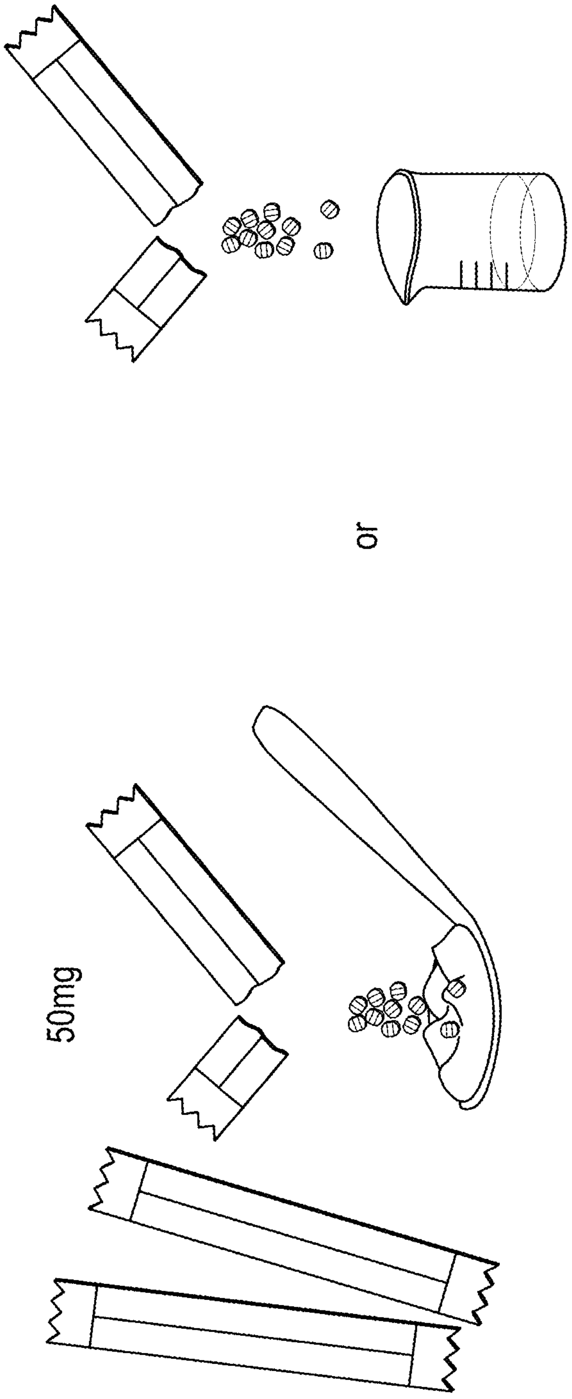
FIG. 7: Example of the use of stickpacks: i.e. sprinkle the minnitablets on a spoon of yoghurt. All publications, patent applications, patents and other references mentioned herein are incorporated by reference in their entirety.

Both amorphous solid dispersions as shown in FIG. 6, are stable on a time scale of hours at 40° C./75% relative humidity but undergo phase separation processes at accelerated stress storage conditions (40° C./75% relative humidity for more than 14 days)

Example 7: Formulation G

Formulation G is an adult formulation that is to be encapsulated in a HPMC size 0 capsule. The composition of formulation G is shown table 7. Formulation G can be made according to WO2019018570.

TABLE 7

Composition of Formulation G

| Component | % w/w | Amount per Capsule (mg) |
|---|---|---|
| Intragranular Components | | |
| N-[5-(3,5-difluorobenzyl)-1H-indazol-3-yl]-4-(4-methyl-piperazin-1-yl)-2-(tetrahydro-2H-pyran-4-ylamino)-benzamide | 44.44 | 200.00 |
| Lactose Anhydrous | 28.89 | 130.00 |
| Hydroxypropyl Methylcellulose | 4.00 | 18.00 |
| Crospovidone | 2.78 | 12.50 |
| Tartaric Acid | 13.11 | 59.00 |
| Magnesium Stearate | 0.56 | 2.50 |
| Extragranular Components | | |
| Microcrystalline Cellulose | 2.97 | 13.37 |
| Crospovidone | 2.50 | 11.25 |
| Colloidal Silicon Dioxide | 0.25 | 1.13 |
| Magnesium Stearate | 0.50 | 2.25 |
| Total | 100.0 | 450.00 |

Example 8: Dissolution of formulation A, B and G

Formulation A, B and G were tested for drug release using the USP Apparatus Type I Basket Method under the conditions described below with a bath temperature of 37° C. and with UV Detection at 300 nm. These formulations were tested using the conditions described herein and provided the dissolution results in table 8 that represent the average percent drug release (based on measured amount of N-[5-(3,5-difluorobenzyl)-1H-indazol-3-yl]-4-(4-methyl-piperazin-1-yl)-2-(tetrahydro-2H-pyran-4-ylamino)-benzamide contained in the media compared to the total amount of N-[5-(3,5-difluorobenzyl)-1H-indazol-3-yl]-4-(4-methyl-piperazin-1-yl)-2-(tetrahydro-2H-pyran-4-ylamino)-benzamide contained in the capsules or tablets.

TABLE 8

Dissolution of formulation A, B and G

| Time in Minutes | Formulation A | Formulation B Means % dissolved | Formulation G |
|---|---|---|---|
| 0 | 0 | 0 | 0 |
| 15 | 85 | 1 | 0 |
| 20 | 87 | 1 | 1 |
| 30 | 88 | 1 | 13 |
| 40 | 89 | 3 | 39 |
| 45 | 90 | 47 | 53 |
| 60 | 90 | 82 | 82 |
| 75 | 95 | 90 | 87 |
| Apparatus | Basket | Basket | Basket |
| Rotation speed | 100 rpm | 100 rpm | 100 rpm |
| Medium | Potassium phosphate butter 50 mM. pH 6.0 + 0.374% Tween 80 | Potassium phosphate butter 50 mM. pH 6.0 + 0.374% Tween 80 | Potassium phosphate butter 50 mM. pH 6.0 + 0.374% Tween 80 |
| Volume | 500 mL | 500 mL | 1000 mL |
| Dose strength | 50 mg | 50 mg | 200 mg |

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The invention claimed is:

1. A pharmaceutical composition comprising:

1) An intragranular layer comprising:
   a) 25 ±5% by weight of N-[5-(3,5-difluorobenzyl)-1H-indazol-3-yl]-4-(4-methyl-piperazin-1-yl)-2-(tetrahydro-2H-pyran-4-ylamino)-benzamide, also known as entrectinib;
   b) between 0.5% and 1.0% by weight of colloidal silicon dioxide;
   c) between 1.0% and 3.0% by weight of sodium stearyl fumarate;
   d) between 2.0% and 6.0% by weight of croscarmellose sodium;
   e) between 20% and 60% by weight of microcrystalline cellulose;
   f) between 4.42% and 10.32% by weight of tartaric acid:
2) An extragranular layer comprising:
   a) between 0.2% and 0.8% by weight of colloidal silicon dioxide;
   b) between 5% and 15% by weight of mannitol;
   c) between 0.25% and 1.0% by weight of magnesium stearate; and
   d) between 1.0% and 3.0% by weight of croscarmellose sodium.

2. The pharmaceutical composition according to claim 1, comprising:

1) An intragranular layer comprising:
   a) 25 ±1% by weight of N-[5-(3,5-difluorobenzyl)-1H-indazol-3-yl]-4-(4-methyl-piperazin-1-yl)-2-(tetrahydro-2H-pyran-4-ylamino)-benzamide, also known as entrectinib;
   b) 0.9±0.10% by weight of colloidal silicon dioxide;
   c) 1.8±0.2% by weight of sodium stearyl fumarate;
   d) 4.5±0.05% by weight of croscarmellose sodium;
   e) 47.5±5% by weight of microcrystalline cellulose;
   f) 7.37±0.5% by weight of tartaric acid;
2. An extragranular layer comprising:
   a) 0.20±0.05% by weight of colloidal silicon dioxide;
   b) 10±1% by weight of mannitol;
   c) 0.45±0.05% by weight of magnesium stearate; and
   d) 2.25±0.05% by weight of croscarmellose sodium.

3. The pharmaceutical composition according to claim 1, wherein the composition only comprises N-[5-(3,5-difluorobenzyl)-1H-indazol-3-yl]-4-(4-methyl-piperazin-1-yl)-2-(tetrahydro-2H-pyran-4-ylamino)-benzamide, also known as entrectinib as the API.

4. The pharmaceutical composition according to claim 1, wherein the composition further comprises a pH independent film coating.

5. The pharmaceutical composition according to claim 1, wherein the composition further comprises a film coating comprising hydroxypropyl cellulose and ethylcellulose.

6. A method for treating cancer in a subject in need thereof, comprising administering a therapeutically effective amount of the pharmaceutical composition according to claim 1, wherein the cancer is a ROS1-positive or NTRK Gene Fusion-positive solid tumor selected from sarcomas and carcinomas.

7. The method of claim 6, wherein the cancer is lung cancer.

* * * * *